(12) United States Patent
Langham

(10) Patent No.: US 9,167,795 B2
(45) Date of Patent: Oct. 27, 2015

(54) NON-DEHISCENT SESAME IND VARIETY SESACO 38

(71) Applicant: Sesaco Corporation, Austin, TX (US)

(72) Inventor: Derald Ray Langham, San Antonio, TX (US)

(73) Assignee: Sesaco Corporation, Austin, TX (US)

( * ) Notice: Subject to any disclaimer, the term of this patent is extended or adjusted under 35 U.S.C. 154(b) by 0 days.

(21) Appl. No.: 14/636,910

(22) Filed: Mar. 3, 2015

(65) Prior Publication Data

US 2015/0264880 A1    Sep. 24, 2015

Related U.S. Application Data

(60) Provisional application No. 61/954,717, filed on Mar. 18, 2014.

(51) Int. Cl.
| | | |
|---|---|---|
| *A01H 5/00* | (2006.01) | |
| *A01H 5/10* | (2006.01) | |
| *A01H 4/00* | (2006.01) | |
| *A01H 1/00* | (2006.01) | |
| *A01H 1/02* | (2006.01) | |

(52) U.S. Cl.
CPC ... *A01H 5/10* (2013.01); *A01H 1/02* (2013.01)

(58) Field of Classification Search
None
See application file for complete search history.

(56) References Cited

U.S. PATENT DOCUMENTS

| | | | |
|---|---|---|---|
| 6,100,452 | A | 8/2000 | Langham |
| 6,781,031 | B2 | 8/2004 | Langham |
| 6,815,576 | B2 | 11/2004 | Langham |
| 7,148,403 | B2 | 12/2006 | Langham |
| 7,332,652 | B2 | 2/2008 | Langham |
| 7,847,149 | B2 | 12/2010 | Langham |
| 7,855,317 | B2 | 12/2010 | Langham |
| 7,964,768 | B2 | 6/2011 | Langham |
| 8,003,848 | B2 | 8/2011 | Langham |
| 8,058,503 | B1 | 11/2011 | Langham |
| 8,080,707 | B2 | 12/2011 | Langham |
| 8,207,397 | B1 | 6/2012 | Langham |
| 8,507,750 | B1 | 8/2013 | Langham |
| 8,586,823 | B1 | 11/2013 | Langham |
| 2006/0230472 | A1 * | 10/2006 | Langham ............ 800/295 |

FOREIGN PATENT DOCUMENTS

| | | |
|---|---|---|
| WO | WO9915681 | 4/1999 |
| WO | WO0013488 | 3/2000 |

OTHER PUBLICATIONS

Ashri, A. 1998. "Seseme Breeding," Plant Breeding Rev. 16:179-228
Ashri, A. 1980. "Sesame," Oil Crops of the World, Chap. 18, pp. 375-387; McGraw-Hill Publishing, Co., New York.
Bakheit, et al. 1996, "Inheritance of Some Qualitative and Quantitative Characters in Sesamum idicum L," Assuit Journal of the Agricultural Sciences 27:27-41.
Day, Jamie. 1998 "The mechanism of indehiscence in Sesame. Features that might be useful in a breeding programme," Third FAO/IAEA Research Coordination meeting on Induced Mutations for Sesame Improvements, Bangkok, Thailand; Apr. 6-19, 1998; 11pp.
Delgado, et al. 1992 "Analisis Del Cruzamiento Dialelico De Seis Variedades Indehiscenes Y Dos Dehiscentes de Ajonjoli Sesamum indicum L." Agronomia Tropical 42:191-210.
Hutson, B.D. 1983. "Standards for the inspection and grading of sesame seed," Hutson Laboratories, Yuma, Arizona, pp. 1-5.
IBPGR Secretariat, 1981, "Descriptor for Sesame," International Board for Plant Genetic Resources, Rome, pp. 1-19.
Kalton, R.R. 1949. "A promising new oilseed crop for Texas," Proc First International Sesame Conference, Clemson Agricultural College, Clemson, South Carolina, pp. 62-66.
Langham, D.R. 2007. "Phenology of Sesame," Issues in New Crops and New Uses, Janick & Whipkey, eds., ASHS Press, Alexandria, VA, pp. 144-182.
Langham, D.G. 1944. "Natural and controlled pollination in sesame," Journal of Heredity 8:254-256.
Langham, D.G. and Rodriguez, J. 1949. "Improvements in Sesame in Venezuela," Proc. First Intern'l Sesame Conf., Clemson Agri. College, Clemson, South Carolina, pp. 74-79.
Langham, et al. 1956. "Dehiscencia Y otras caracteristicas del ajonjoli, Sesamum indicum L., en relacion con el problema de la cosecha," Gensa, Maracay, Venezuela; pp. 3-16.
Langham, D.R. 1998. "Shatter resistance in Sesame," Third FAO/IAEA Res. Co-ord. Mtng on Induced Mutations for Sesame Improvements, Bangkok, Thailand, Apr. 6-10, 1998; 14 pages.
Langham D.R. 2001. "Shatter resistance in sesame" In: L. Van Zanten (ed.), Sesame improvements by induced mutations, Proc. Final FAO/IAEA Coordination Research Meeting, IAEA, Vienna TECDOC 1195, pp. 51-61.
Langham, D.R. & Vimers, T. 2002. "Progress in mechanizing sesame in the U.S. through breeding," Trends in Crops and New Uses, J. Janick & A. Whipkey (eds.), ASHA Press Alexandria, VA; pp. 157-173.
Namiki, Mitsuo. 1995. "The Chemistry and Physiological Functions of Sesame," Food Reviews International, 11:281-329.
Osman, H.E. 1985. "Studies in sesame: hybridization and related techiniques," FAO Plant Production and Protection Paper No. 66, pp. 145-156.

(Continued)

*Primary Examiner* — Vinod Kumar

(74) *Attorney, Agent, or Firm* — D. Scott Hemingway; Hemingway & Hansen, LLP

(57) ABSTRACT

Non-dehiscent sesame (*Sesamum indicum* L.) (IND) designated Sesaco 38 (S38) is herein disclosed. Its degree of shatter resistance, or seed retention, makes S38 suitable for mechanized harvesting and for selection for sesame crop growth in most geographical locations.

9 Claims, 13 Drawing Sheets

(56) References Cited

OTHER PUBLICATIONS

"Recommendations for the Discussion Groups," 1995. Proceedings of Sesame Workshop, Darwin and Katherine, Northern Territory, Australia, Mar. 12-23, 1995, pp. 252-257.
Shigeo, et al. 1994. "Breeding of good quality sesame with dehiscence resistance and strong antioxidative property," Baiorunessansu Keikaku (abstract only).
Wongyai, W. & Juttpornpong, S. 1992 Indirect selection for seed weight in sesame using capsule size as a criteria, Sesame and Safflower Newsletter, No. 7, pp. 4-7.
Weiss, E.A. 1971. "History," Castor, Sesame and Safflower, Leonard-Hill Books, London; pp. 311-525.
Weiss, E.A. 1983. "Sesame," Oilseed Crops, Longman Inc., New York, pp. 282-340.
Weiss. 2000. "Sesame," Oilseed Crops, Longman Inc., New York, pp. 131-164.
Yermanos, D.M. 1980. "Sesame," Hybridization of Crop Plants, American Society of Agronomy—Crop Science of America, Madison, Wisconsin, pp. 549-563.
Yermanos, D.M. 1984. "Sesame growing: an idealized overview," Text of speech given in Cairo. Egypt, 4 pages.
Zanten, L.Van (ed.) 1996. "Conclusions and Recommendations," 2nd FAO/IAEA Research Coordination Meeting, Antalya, Turkey, pp. 107-113.

* cited by examiner

TO FIG. 1B

NON-DEHISCENT SESAME IND VARIETY SESACO 38

CROSS REFERENCE TO RELATED APPLICATIONS

This application claims the benefit of U.S. Provisional Application No. 61/954,717 filed Mar. 18, 2014.

STATEMENT REGARDING FEDERALLY SPONSORED RESEARCH OR DEVELOPMENT

Not applicable.

TECHNICAL FIELD

This invention relates to a new *Sesamum indicum* L. variety with improved non-dehiscence (IND) appropriate for mechanized harvesting.

BACKGROUND OF THE INVENTION

Sesame, or *Sesamum indicum*, is a tropical annual cultivated worldwide for its oil and its nut flavored seeds. The sesame plant grows to a height of about 52-249 cm, and at its leaf axils are found capsules, which contain the sesame seed. Upon maturity in nature, the capsules holding the sesame seeds begin to dry down, the capsules normally split open, and the seeds fall out. Commercially, the harvester tries to recover as much seed as possible from mature capsules. From ancient times through the present, the opening of the capsule has been the major factor in attempting to successfully collect the seed. Harvesting methods, weather, and plant characteristics all contribute to the amount of seed recovered.

The majority of the world's sesame is harvested manually. With manual non-mechanized methods, it is desirable for the sesame seed to fall readily from the plant. Manual harvesting is labor intensive. Efforts to mechanize or partially mechanize harvesting met with limited success.

A breakthrough was accomplished when non-dehiscent (ND) sesame was developed and patented by Derald Ray Langham. ND sesame was found to possess the proper characteristics, which would enable mechanical harvesting without the seed loss disadvantages reported with prior varieties.

U.S. Pat. Nos. 6,100,452; 6,815,576; 6,781,031; 7,148,403; 7,332,652; and 8,003,848 each disclose and claim non-dehiscent (ND) sesame cultivars having various characteristics.

U.S. Pat. Nos. 7,847,149; 7,855,317; 7,964,768; 8,058,503; 8,080,707; 8,207,397; 8,507,750; 8,581,026; and 8,586,823 each disclose and claim improved non-dehiscent (IND) sesame cultivars having various characteristics.

SUMMARY OF THE INVENTION

A new sesame variety designated Sesaco 38 (S38) with representative seed having been deposited on Mar. 14, 2014 with the American Type Culture Collection (ATCC) Patent Depository under ATCC Accession No. PTA-121090. In one aspect, the invention comprises a seed of sesame variety designated S38, a sample of said seed having been deposited under ATCC Accession No. PTA-121090. In another aspect, the invention comprises a sesame plant produced by growing the seed of sesame variety S38, a sample of said seed having been deposited under ATCC Accession No. PTA-121090.

In yet another aspect, the invention comprises plant cells derived from a sesame plant, said plant produced by growing the seed of sesame variety S38, a sample of said seed having been deposited under ATCC Accession No. PTA-121090. The plant cells may be selected, for example, from pollen, tissue culture of regenerable cells, and asexually reproducing cultivars.

In yet another aspect, the invention comprises a sesame plant having all the physiological and morphological characteristics of sesame variety S38, a sample of the seed of said variety having been deposited under ATCC Accession No. PTA-121090.

In another aspect, the invention comprises a sesame plant regenerated from a tissue culture of regenerable cells produced from plant cells derived from sesame variety S38, a sample of said seed having been deposited under ATCC Accession No. PTA-121090, wherein said regenerated sesame plant has all the physiological and morphological characteristics of said sesame variety S38. The plant cells may be derived from S38 seeds or plant cells from tissue from a sesame plant produced by growing the seed of sesame variety S38.

In another aspect, the invention comprises a method of producing sesame seed, comprising crossing a first parent sesame plant with a second parent sesame plant and harvesting the resultant sesame seed, wherein said first or second parent sesame plant was produced by growing seed of sesame variety S38, a sample of said seed having been deposited under ATCC Accession No. PTA-121090.

BRIEF DESCRIPTION OF THE DRAWINGS

FIG. 2 depicts a comparison of the percent of seed retention during Shaker Shatter Resistance testing from 1997 to 2011 for the various Sesaco sesame varieties.

FIG. 3 depicts a comparison of the mean improved non-dehiscent visual rating for the various Sesaco sesame varieties grown under similar conditions.

FIG. 4 depicts a comparison of the composite kill tolerance ratings for the various Sesaco sesame varieties grown under similar conditions.

FIG. 5 depicts a comparison of the mean days to physiological maturity for the various Sesaco sesame varieties grown under similar conditions.

FIG. 6 depicts a comparison of the yield at drydown for the various Sesaco sesame varieties grown under similar conditions.

FIG. 7 depicts a comparison of the mean weight of 100 seeds in grams from 1997 to 2011 for the various Sesaco sesame varieties.

FIG. 8 depicts a comparison of seed oil content for the various Sesaco sesame varieties grown under similar conditions.

FIG. 9 depicts a comparison of whitefly tolerance for the various Sesaco varieties of sesame plants grown under similar conditions.

FIG. 10 depicts a comparison of leaf disease tolerance for the various Sesaco varieties of sesame plants grown under similar conditions.

DETAILED DESCRIPTION

Figure 1A:
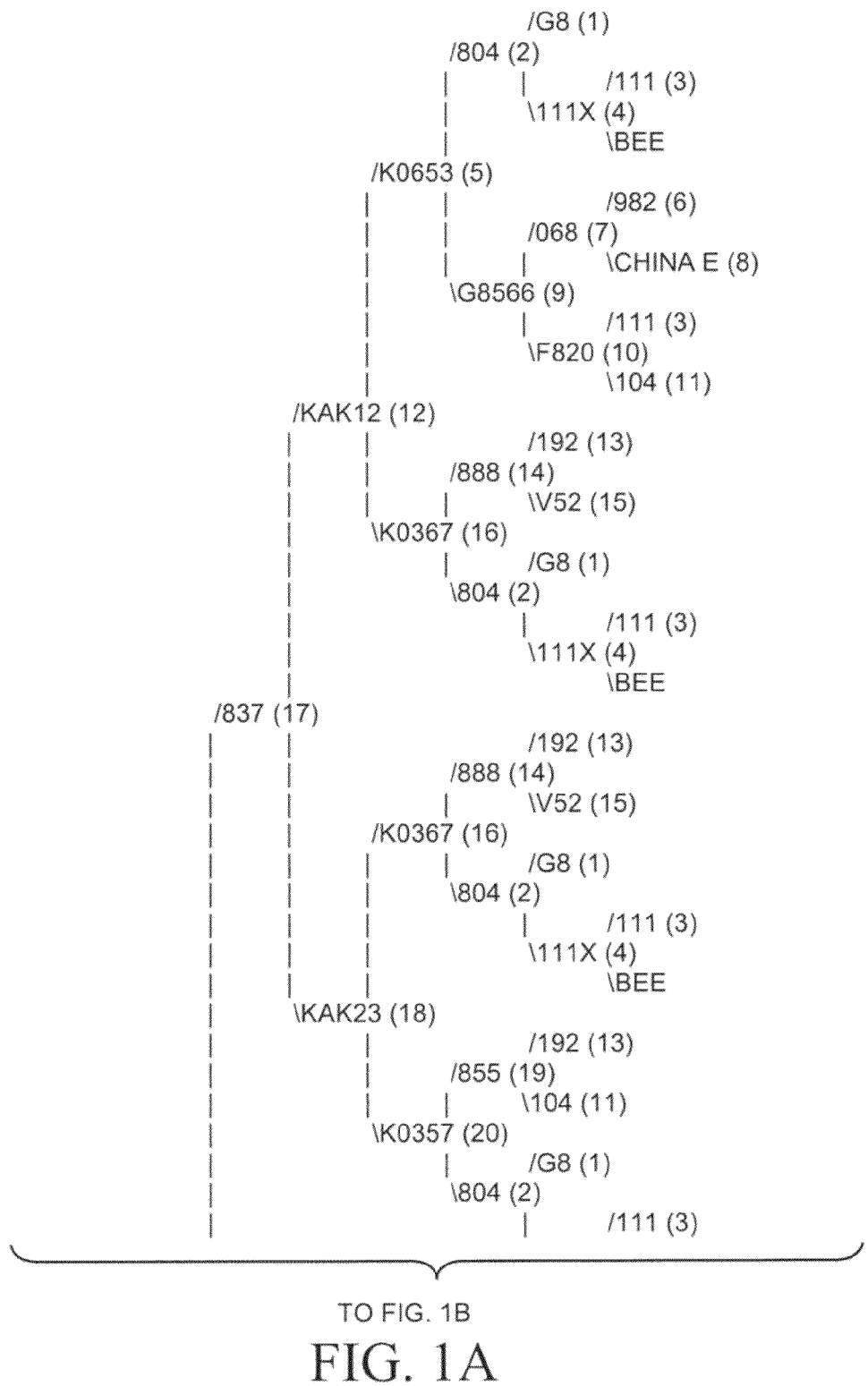
FIG. 1A-1D depicts the lineage of S38.
Figure 1B:
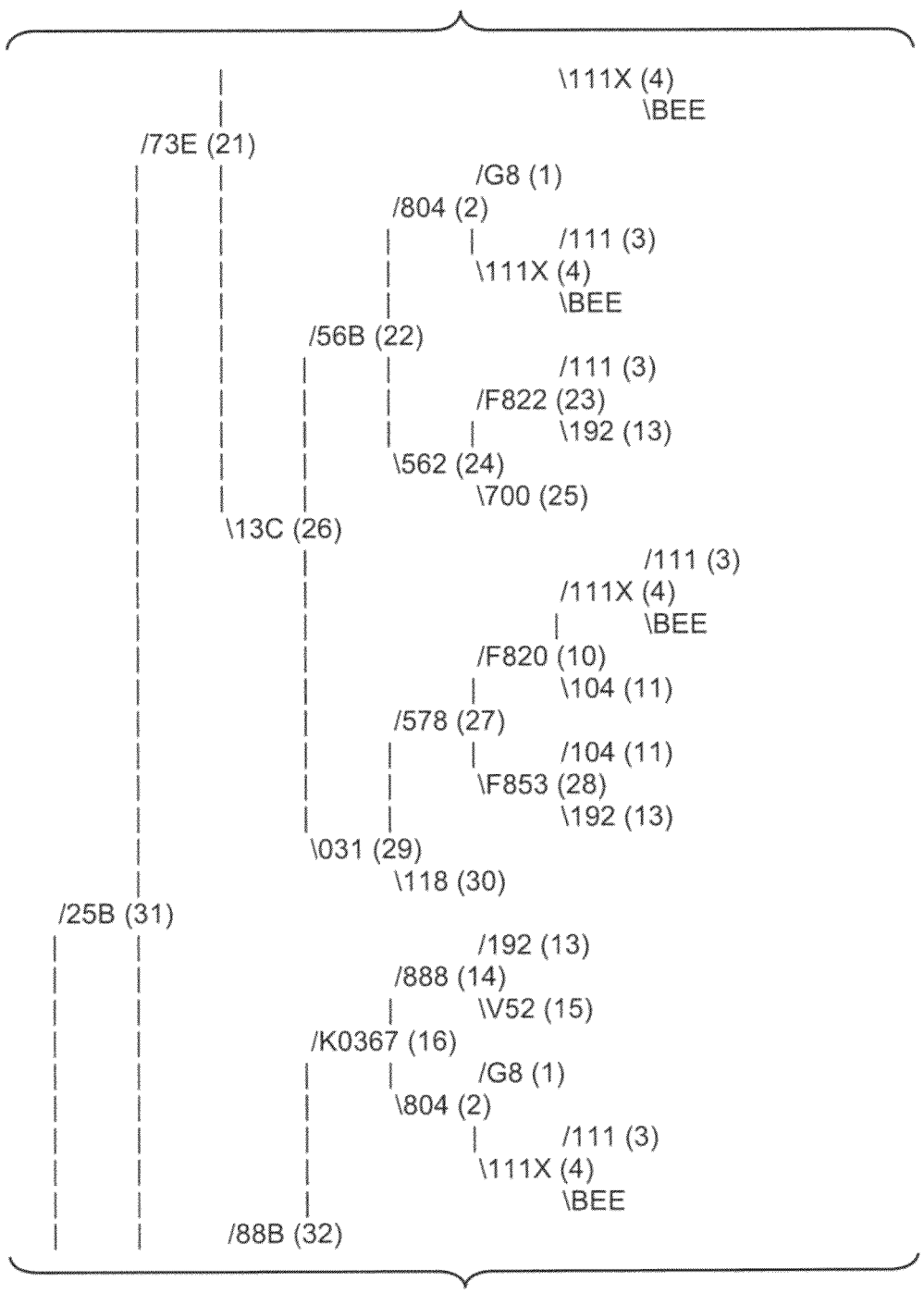
Figure 1C:
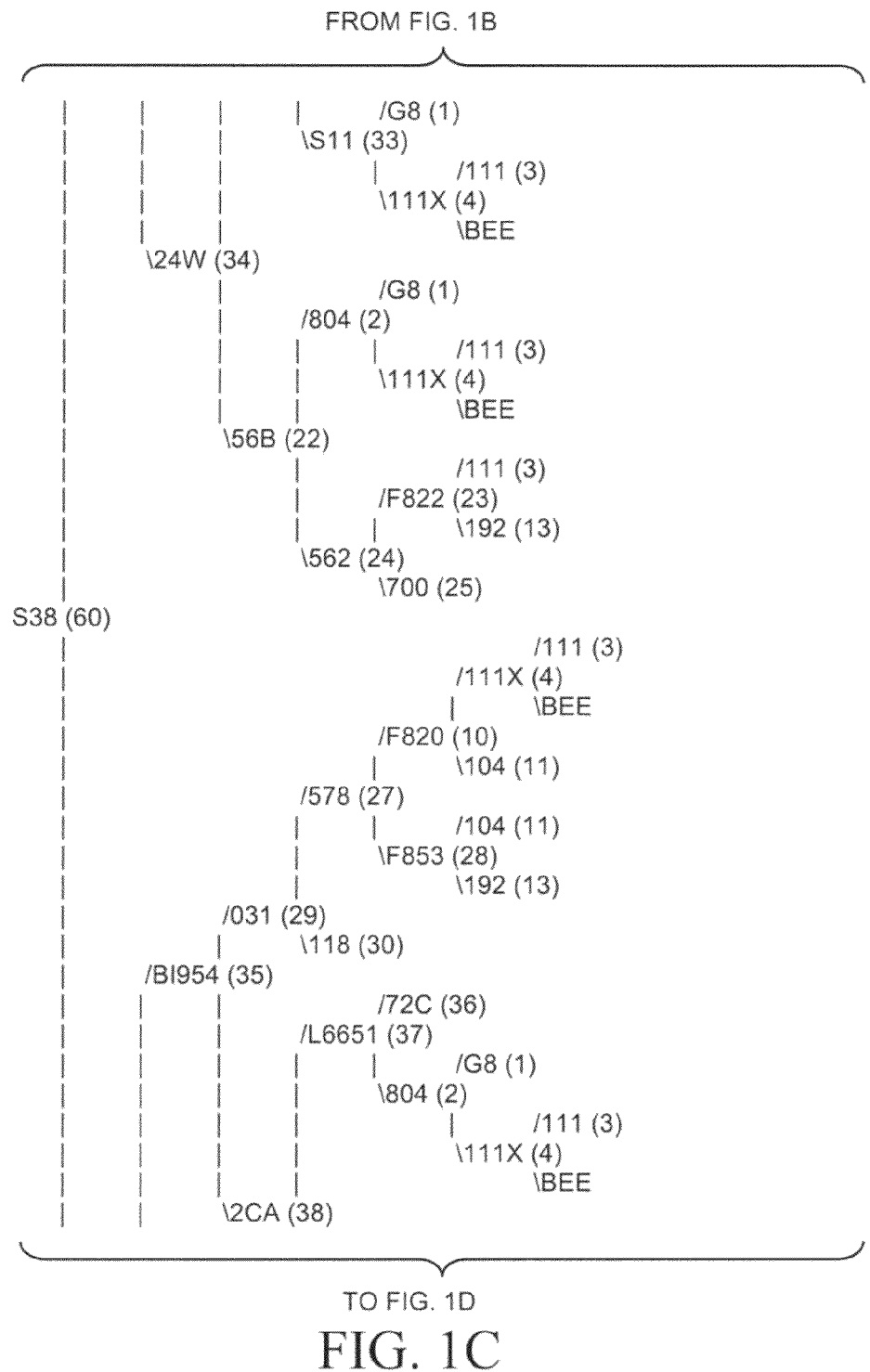
Figure 1D:
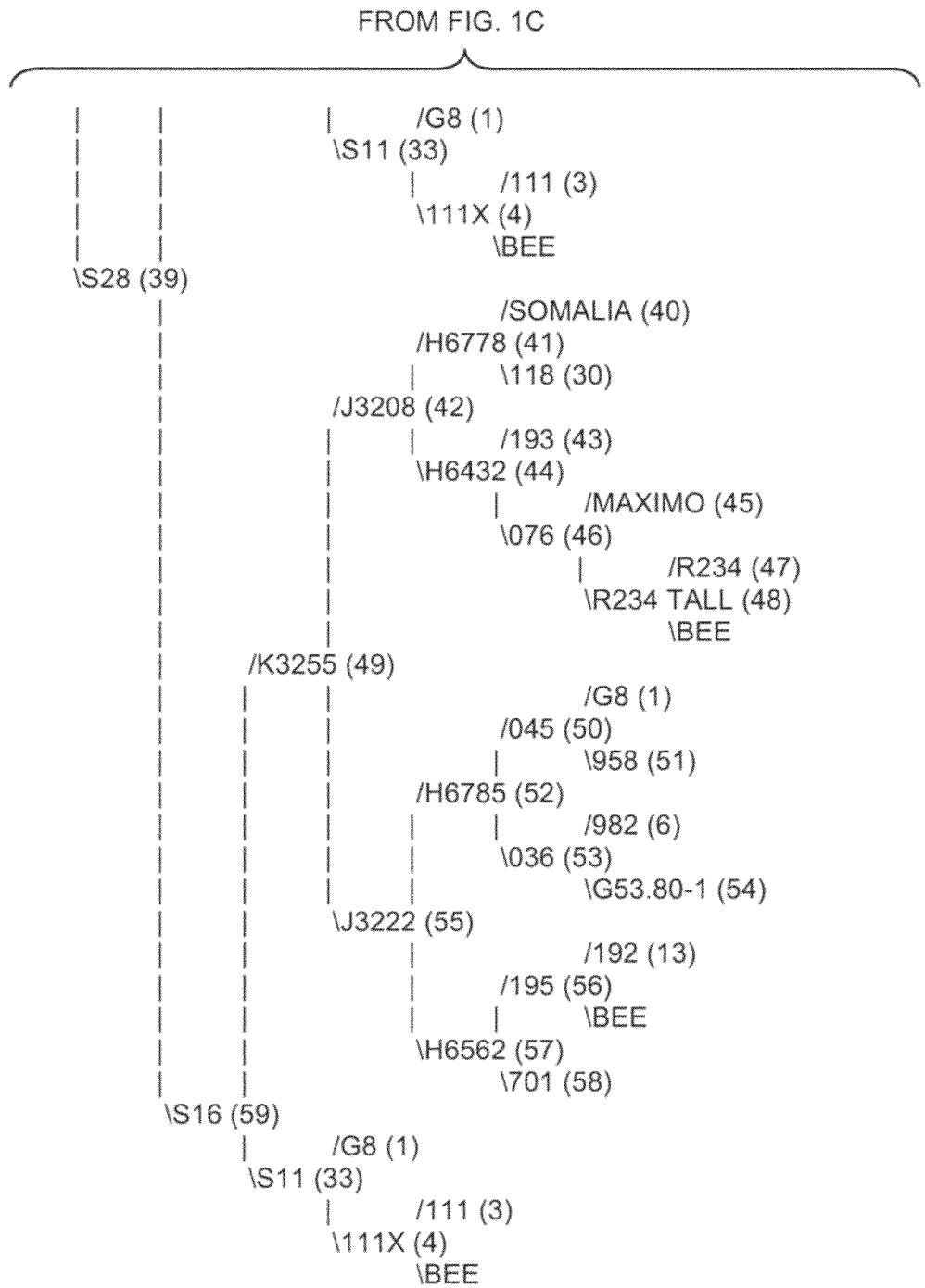

Herein disclosed is a Non-Dehiscent (ND) sesame variety designated Sesaco 38 (S38), which exhibits Improved Non- Dehiscence (IND) and novel characteristics which make it a commercially suitable sesame line. By virtue of having IND, there is less seed loss when left in the field past prime harvest time in adverse weather conditions, for example, rain, fog, dew, and wind. S38 is suitable for mechanical harvesting.

The Improved Non-Dehiscent (IND) class of sesame, developed by Derald Ray Langham, is ND, but IND sesame also exhibits better adhesion between false membranes and improved placenta attachment. IND sesame holds more seed than prior sesame types, as measured four weeks after a crop is ready for harvest (could have been combined). IND characteristics offer advantages for certain growing applications.

Compared to ND sesame, IND sesame has more seed in the capsules when measured between 4 and 9 weeks after the ideal harvest time.

Without wishing to be bound by one particular theory, it is believed that this increased amount of seed in the capsules may be due to the S38 variety having the ability to better withstand adverse environmental conditions such as inclement or harsh weather. Examples of adverse weather conditions to which S38 has been subjected in this regard are rain, fog, dew, and wind. S38 variety has been tested and meets the criteria of IND.

U.S. Pat. No. 8,080,707 is herein incorporated by reference as if fully set forth herein. This application discloses Improved Non-Dehiscent Sesame. S38 is an example of a variety which resulted from breeding methods described therein.

S38 exhibits improved shatter resistance, acceptable tolerance to common fungal diseases, and a maturity that allows a wide geographical range. Further, S38 exhibits higher yield in geographical locations desirable for sesame planting, and exhibits desirable seed size and seed color. S38 is suitable for planting in areas that have approximately a 21° C. ground temperature when planted in the spring and night temperatures above 5° C. for normal termination. An exemplary desirable geographical area for S38 is from South Texas at the Rio Grande to Central Kansas and to the Caprock at elevations below 1,000 meters eastward to the Atlantic Ocean. Other exemplary areas are areas of the United States or of the world, which areas have similar climatic conditions, daylength patterns (similar latitudes) and elevations.

In describing the present invention, it is helpful to be aware of some terminology. Sesame plants have been studied for their response to seasonal and climatic changes and the environment in, which they live during the different phases and stages of growth and development. This type of study, called "phenology" has been documented by the inventor in Langham, D. R. 2007. "Phenology of sesame," In: J. Janick and A. Whipkey (ed.), Issues in New Crops and New Uses, ASHS Press, Alexandria, Va.

Table I summarizes the phases and stages of sesame, and will be useful in describing the present invention.

TABLE I

Phases and stages of sesame

| Stage/Phase | Abbreviation | End point of stage | No. $DAP^Z$ weeks |
|---|---|---|---|
| Vegetative | VG | | |
| Germination | GR | Emergence | 0-5 1− |
| Seedling | SD | $3^{rd}$ pair true leaf length = $2^{nd}$ | 6-25 3− |
| Juvenile | JV | First buds | 26-37 1+ |
| Pre-reproductive | PP | 50% open flowers | 38-44 1− |
| Reproductive | RP | | |

TABLE I-continued

Phases and stages of sesame

| Stage/Phase | Abbreviation | End point of stage | No. $DAP^Z$ weeks |
|---|---|---|---|
| Early bloom | EB | 5 node pairs of capsules | 45-52 1 |
| Mid bloom | MB | Branches/minor plants stop flowering | 53-81 4 |
| Late bloom | LB | 90% of plants with no open flowers | 82-90 1+ |
| Ripening | RI | Physiological maturity (PM) | 91-106 2+ |
| Drying | DR | | |
| Full maturity | FM | All seed mature | 107-112 1− |
| Initial drydown | ID | $1^{st}$ dry capsules | 113-126 2 |
| Late drydown | LD | Full drydown | 127-146 3 |

$^Z$DAP = days after planting. These numbers are based on S26 in 2004 Uvalde, Texas, under irrigation.

There are several concepts and terms that are used in this document that should be defined. The Environmental Protection Agency has allowed harvest aids to be used to desiccate sesame within 2 weeks of application after physiological maturity. If no harvest aids are used, in the initial drydown stage in Table I, the capsules begin to dry and open. This stage ends when 10% of the plants have one or more dry capsules. The late drydown stage ends when the plants are dry enough so that upon harvest, the seed has a moisture content of 6% or less. At this point some of the capsules have been dry for 5 weeks in the example used in Table I, but in other environments for other varieties, the drying can stretch to 7 weeks. The "ideal harvest time" is at the end of the late drying stage. At this point, a combine (also sometimes referred to as a combine harvester, a machine that combines the tasks of harvesting, threshing, and cleaning grain crops) can be used to cut and thresh the plants and separate the seed from the undesired plant material. However, at times, weather may prevent harvest at the ideal time. The plants may have to remain in the field for as much as an additional four weeks, and in some cases even longer. Thus, time $t_0$ corresponds to the ideal harvest time and time $t_1$, which corresponds to the time the grower actually harvests the sesame, is a time later than time $t_0$.

The pedigree method of plant breeding was used to develop S38. Sesame is generally self-pollinated. Crossing is done using standard techniques as delineated in Yermanos, D. M. 1980. "Sesame. Hybridization of crop plants," *Am Soc. Agronomy-Crop Sci. of America*, pp. 549-563 and U.S. Pat. No. 6,100,452. Ashri provides an overview of sesame breeding in Ashri, A. (1998). "Sesame breeding," *Plant Breed. Rev.* 16:179-228 and Ashri, A. 2007. Sesame (*Sesamum indicum* L.). In: R. J. Singh, Ed., Genetic Resources, Chromosome Engineering, and Crop Improvement, Vol. 4, Oilseed Crops, p. 231-289, CRC Press, Boca Raton, Fla., USA.

The lineage of S38 is presented in FIG. 1. G8 (1) was a line obtained from D. G. Langham in 1977 and first planted by Sesaco in the Kamman nursery (Wellton, Ariz.) in 1978. It was a selection from the cultivar 'Guacara', which D. G. Langham developed in Venezuela in the 1950s. Guacara was an initial selection from a cross that later produced one of the major varieties in Venezuela-Aceitera. Within Sesaco, G8 first carried the identifier X011 and was later changed to TG8.

804 (2) was a cross made by Sesaco between G8 (1) and 111X (4) in the Nickerson nursery (Yuma, Ariz.) in 1982.

Within Sesaco, it has carried the identifier F804; in 1988, a selection of this line became Sesaco 11 (S11).

111 (3) was a line obtained from the NPGS (PI1173955) in 1979 and first planted by Sesaco in the Woods nursery (Wellton, Ariz.) in 1981. NPGS obtained it in 1949 from W. N. Koelz, USDA, Beltsville, Md., who obtained it from India. Within Sesaco, 111 first carried the identifier 0858 and was then changed to X111. In 1985, a selection of this line became Sesaco 4 (S04).

111X (4) was an outcross in the 111 (3) plot BT0458 in the Nickerson nursery (Yuma, Ariz.) in 1982. Within Sesaco, it carried the identifier E0745 and was later changed to T111X.

K0653 (5) was a cross made by Sesaco between 804 (2) and G8566 (9) in the Hancock nursery (Wellton, Ariz.) in 1986. Within Sesaco, it carried the identifier K3255.

982 (6) was a line obtained from the *Sesamum* Foundation in 1977 and first planted in the Kamman nursery (Wellton, Ariz.) in 1978. It was obtained with a designator of SF477 and was named G53.98-2. The *Sesamum* Foundation obtained it from John Martin in 1962 who had obtained it from the D. G. Langham breeding program in Venezuela. G53.98-2 was a cross made by D. G. Langham in 1953 in Guacara, Venezuela. Within Sesaco, 982 carried the identifier 0477 and then changed to T982.

068 (7) was a cross made by Sesaco between 982 (6) and CHINA E (8) in the Kamman nursery (Wellton, Ariz.) in 1979. Within Sesaco, it carried the identifier C068 and was later changed to T068.

CHINA E (8) was a line obtained from the NPGS (PI 158072) in 1979 and first planted by Sesaco in the Woods nursery (Wellton, Ariz.) in 1981. Within Sesaco, CHINA E first carried the identifier 0765 and was then changed to TCHE.

G8566 (9) was a cross made by Sesaco between 068 (7) and F820 (10) in the McElhaney nursery (Wellton, Ariz.) in 1983. Within Sesaco it carried the identifier G8566.

F820 (10) was a cross made by Sesaco between 111 (3) and 104 (11) in the Nickerson nursery (Yuma, Ariz.) in 1982. Within Sesaco, it carried the identifier F820.

104 (11) was a line obtained from the *Sesamum* Foundation (D. G. Langham, Fallbrook, Calif.) in 1977 and first planted in the Kamman nursery (Wellton, Ariz.) in 1978. It was obtained with the designator SF084. The *Sesamum* Foundation obtained it from Maximo Rodriguez in 1961. He had collected it from Mexico where it was known as Instituto 8. Instituto 8 was a selection from G53.48, a cross made by D. G. Langham in 1953 in Guacara, Venezuela. Within Sesaco, 104 carried the identifier 0084. In 1983, a selection of this line became Sesaco 2 (S02)

KAK12 (12) was a cross made by Sesaco between K0653 (5) and K0367 (16) in the Langham greenhouse (Yuma, Ariz.) in 1986-87. Within Sesaco, it carried the identifier KAK12.

192 (13) was a line obtained from the M. L. Kinman in 1980 and first planted by Sesaco in the Woods nursery (Wellton, Ariz.) in 1981. The line was originally T61429-B-4-1-3 from the Kinman USDA sesame program, College Station, Tex., which had been in cold storage at Ft. Collins, Colo. In 1997, the line was transferred to the NPGS, Griffin, Ga. and given the identifier PI599462. Within Sesaco, 192 first carried the identifier 1479 and then was changed to X191 and X193. In 1985, a selection from X193 became Sesaco 3 (S03) and a selection of X191 became Sesaco 7 (S07).

888 (14) was a cross made by Sesaco between 192 (13) and V52 (15) in the Nickerson nursery (Yuma, Ariz.) in 1982. Within Sesaco, 888 first carried the identifier F888 and was later changed to T888.

V52 (15) was a cultivar designated as SF075 obtained from the *Sesamum* Foundation (D. G. Langham, Fallbrook, Calif.) collection in 1977 and first planted by Sesaco in the Kamman nursery (Wellton, Ariz.) in 1978. The *Sesamum* Foundation obtained it from B. Mazzani (Maracay, Venezuela) in 1960. Originally, it was a cultivar known as Venezuela 52 developed by D. G. Langham in the 1940s. Within Sesaco, V52 first carried the identifier 0075 and was later changed to TV52.

K0367 (16) was a cross made by Sesaco between 888 (14) and 804 (2) in the Hancock nursery (Wellton, Ariz.) in 1986. Within Sesaco, it carried the identifier K0367.

837 (17) was a cross made by Sesaco between KAK12 (12) and KAK23 (18) in the Wright nursery (Tacna, Ariz.) in 1987. Within Sesaco, it carried the identifier L0475, and later became X837 and then T837.

KAK23 (18) was a cross made by Sesaco between K0367 (16) and K0357 (20) in the Langham greenhouse (Yuma, Ariz.) in 1986-87. Within Sesaco, it carried the identifier KAK23.

855 (19) was a cross made by Sesaco between 192 (13) and 104 (11) in the Nickerson nursery (Yuma, Ariz.) in 1982. Within Sesaco, it carried the identifier F855; in 1988, a selection of this line became Sesaco 10 (S10).

K0357 (20) was a cross made by Sesaco between 855 (19) and 804 (2) in the Hancock nursery (Wellton, Ariz.) in 1986. Within Sesaco, it carried the identifier K3255.

73E (21) was a cross made by Sesaco between 837 (17) and 13C (26) in the Gilleland nursery (Uvalde, Tex.) in 1995. Within Sesaco, it carried the identifier DN334 and then changed to X73E and then T73E.

56B (22) was a cross made by Sesaco between 804 (2) and 562 (24) in the Wright nursery (Tacna, Ariz.) in 1987. Within Sesaco, it first carried the identifier KAN00 and was later changed to X56B and then to T56B.

F822 (23) was a cross made by Sesaco between 111 (3) and 192 (13) in the Nickerson nursery (Yuma, Ariz.) in 1982. Within Sesaco, it carried the identifier F822.

562 (24) was a cross made by Sesaco between F822 (23) and 700 (25) in the McElhaney nursery (Wellton, Ariz.) in 1983. Within Sesaco, it first carried the identifier G8562 and was later changed to T562.

700 (25) was a line obtained from the NPGS (PI292144) in 1979 and first planted by Sesaco in the Woods nursery (Wellton, Ariz.) in 1981. NPGS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from India and Pakistan. Within Sesaco, 700 first carried the identifier 0700 and was later changed to T700.

13C (26) was a cross made by Sesaco between 56B (22) and 031 (29) in the Sharp nursery (Tacna, Ariz.) in 1990. Within Sesaco it first carried the identifier PF270 and later was changed to X13C and then T13C.

578 (27) was a cross made by Sesaco between F820 (10) and F853 (28) in the McElhaney nursery (Wellton, Ariz.) in 1983. Within Sesaco, it first carried the identifier G8578 and was later changed to T578.

F853 (28) was a cross made by Sesaco between 104 (11) and 192 (13) in the Nickerson nursery (Yuma, Ariz.) in 1982. Within Sesaco, it carried the identifier F853.

031 (29) was a cross made by Sesaco between 578 (27) and 118 (30) in the Ramsey nursery (Roll, Ariz.) in 1984. Within Sesaco, it carried the identifier H0031 and then changed to T031.

118 (30) was a line obtained from the NGPS (PI425944) in 1979 and first planted in Kamman nursery (Wellton, Ariz.) in 1979. The NGPS obtained it in 1978 from P. F. Knowles, University of California, Davis, Calif., who collected it in Pakistan. Within Sesaco, it carried the identifier 1118, which was changed to X118 and then to T118.

25B (31) was a cross made by Sesaco between 73E (21) and 24W (34) in the Gilleland nursery (Uvalde, Tex.) in 1999. Within Sesaco, it carried the identifier HG104, then changed to YG104, then X25B, and finally T25B.

88B (32) was a cross made by Sesaco between K0367 (16) and S11 (33) in the Wright nursery (Tacna, Ariz.) in 1987. Within Sesaco, it first carried the identifier KAC32 and was later changed to X88B and then to T88B.

S11 (33) was a cross made by Sesaco between G8 (1) and 111X (4) in the Nickerson nursery (Yuma, Ariz.) in 1982. Within Sesaco, it has carried the identifier F804. In 1988, a selection of this line became Sesaco 11 (S11).

24W (34) was a cross made by Sesaco between 88B (32) and 56B (22) in the Sharp nursery (Tacna, Ariz.) in 1989. Within Sesaco, it first carried the identifier N2248. In 2000, a selection of this line became Sesaco 25 (S25)—U.S. Pat. No. 6,815,576.

BI1954 (35) was a cross made by Sesaco between 031 (29) and 2CA (38) in the Gilleland nursery (Uvalde, Tex.) in 1993. Within Sesaco, it carried the identifier BI1954.

72C (36) was a line obtained from the NGPS (PI292146) in 1979 and first planted in Woods nursery (Wellton, Ariz.) in 1981. The NGPS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from the Indian subcontinent. Within Sesaco, it has carried the identifier 0702 and then changed to X702. When the selection was made, it carried the designator X702C and later changed to 72C. In 1986, a selection from 72C became Sesaco 12 (S12).

L6651 (37) was a cross made by Sesaco between 72C (36) and 804 (2) in the Wright nursery (Roll, Ariz.) in 1987. Within Sesaco, it carried the identifier L6651.

2CA (38) was a cross made by Sesaco between L6651 (37) and S11 (33) in the Wright nursery (Roll, Ariz.) in 1988. Within Sesaco, it has carried the identifier LCX02 and later changed to X2CA and then to T2CA.

S28 (39) was a cross made by Sesaco between BI1954 (35) and S16 (59) in the Friesenhahn nursery (Knippa, Tex.) in 1994. The original designator was CM764 and later changed to X13J and then to X26B. In 2004, a selection from X26B became Sesaco 28 (S28), U.S. Pat. No. 7,148,403.

SOMALIA (40) was a line obtained from the NGPS (PI210687) in 1979 and first planted in Kamman nursery (Wellton, Ariz.) in 1979. The NGPS obtained it from the Administrazione Fiduciaria Italiana della Somalia, Mogadishu, Somalia. Within Sesaco, it carried the identifier 0730.

H6778 (41) was a cross made by Sesaco between SOMALIA (40) and 118 (30) in the Hancock nursery (Wellton, Ariz.) in 1984. Within Sesaco, it carried the identifier H6778.

J3208 (42) was a cross made by Sesaco between H6778 (41) and H6432 (44) in the Hancock nursery (Wellton, Ariz.) in 1985. Within Sesaco, it carried the identifier J3208.

193 (43) was a selection from 192 (6), which was a line obtained from the M. L. Kinman in 1980 and first planted by Sesaco in the Woods nursery (Wellton, Ariz.) in 1981. The line was originally T61429-B-4-1-3 from the Kinman USDA sesame program, College Station, Tex., which had been in cold storage at Ft. Collins, Colo. In 1997, the line was transferred to the NPGS, Griffin, Ga. and given the identifier PI599462. Within Sesaco, 192 first carried the identifier 1479 and then was changed to X191 (single capsule) and X193 (triple capsule). In 1985, a selection from X193 became Sesaco 3 (S03) and a selection of X191 became Sesaco 7 (S07).

H6432 (44) was a cross made by Sesaco between 193 (43) and 076 (46) in the Hancock nursery (Wellton, Ariz.) in 1984. Within Sesaco, it carried the identifier H6432.

MAXIMO (45) was a line obtained from the *Sesamum* Foundation (D. G. Langham, Fallbrook, Calif.) in 1977 and first planted in the Kamman nursery (Wellton, Ariz.) in 1978. The *Sesamum* Foundation obtained it from Maximo Rodriguez in 1961. He had collected it from Mexico where it was known as Instituto Regional Canasta. Within Sesaco, it carried the identifier 0116 and then changed to TMAX.

076 (46) was a cross made by Sesaco between MAXIMO (45) and R234 TALL (48) in the Kamman nursery (Wellton, Ariz.) in 1979. Within Sesaco, it carried the identifier C076 and then changed to T076.

R234 (47) was a named variety obtained from D. M. Yermanos in 1978 from his sesame program at the University of California at Riverside. It was first planted in the Kamman nursery (Wellton, Ariz.) in 1978. Within Sesaco, it carried the identifier 0544 and then changed to T234.

R234 TALL (48) was an outcross found in a population of R234 (47) in the Kamman nursery (Wellton, Ariz.) in 1979. Within Sesaco, it carried the identifier X026.

K3255 (49) was a cross made by Sesaco between J3208 (42) and J3222 (55) in the Hancock nursery (Wellton, Ariz.) in 1986. Within Sesaco, it carried the identifier K3255.

045 (50) was a cross made by Sesaco between G8 (1) and 958 (51) in the Kamman nursery (Wellton, Ariz.) in 1978. Within Sesaco, it carried the identifier B045 and then changed to T045.

958 (51) was a line obtained from the *Sesamum* Foundation in 1977 and first planted in the Kamman nursery (Wellton, Ariz.) in 1978. It was obtained with a designator of SF411. The *Sesamum* Foundation obtained it from John Martin in 1962 who had obtained it from the D. G. Langham breeding program in Venezuela. Within Sesaco, G958-1 carried the identifier 0411 and later changed to T958.

H6785 (52) was a cross made by Sesaco between 045 (50) and 036 (53) in the Hancock nursery (Wellton, Ariz.) in 1984. Within Sesaco, it carried the identifier H6785.

036 (53) was a cross made by Sesaco between 982 (6) and G53.80-1 (54) in the Kamman nursery (Wellton, Ariz.) in 1979. Within Sesaco, it carried the identifier C036 and then X036. In 1984, a selection from X036 became Sesaco 6 (S06).

G53.80-1 (54) was a line obtained from the *Sesamum* Foundation in 1977 and first planted in the Kamman nursery (Wellton, Ariz.) in 1978. It was obtained with a designator of SF471. The *Sesamum* Foundation obtained it from John Martin in 1962 who had obtained it from the D. G. Langham breeding program in Venezuela. G53.80-1 was a cross made by D. G. Langham in 1953 in Guacara, Venezuela. Within Sesaco, G53.80-1 carried the identifier 0471.

J3222 (55) was a cross made by Sesaco between H6785 (52) and H6562 (57) in the Hancock nursery (Wellton, Ariz.) in 1982. Within Sesaco, it carried the identifier J3222.

195 (56) was an outcross selected in plot MN4584 in a population of 192 (13) in the McElhaney nursery (Wellton, Ariz.) in 1983. Within Sesaco, it carried the identifier E0690 and then changed to X195.

H6562 (57) was a cross made by Sesaco between 195 (56) and 701 (58) in the Hancock nursery (Wellton, Ariz.) in 1984. Within Sesaco, it carried the identifier H6562.

701 (58) was a line obtained from the NGPS (PI292145) in 1979 and first planted in Woods nursery (Wellton, Ariz.) in 1981. The NGPS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from the Indian subcontinent. Within Sesaco, it carried the identifier 0701 and then changed to X701. In 1984, a selection from X701 became Sesaco 5 (S05).

S16 (59) was a cross made by Sesaco between K3255 (49) and S11 (33) in the Wright nursery (Roll, Ariz.) in 1987. Within Sesaco, it carried the identifier KAP11 and then changed to XFXA. In 1991, a selection from XFXA became Sesaco 16 (S16).

S38 (60) was a cross made by Sesaco between 25B (31) and S28 (59) in the Gilleland nursery (Uvalde, Tex.) Year 1 (hereinafter "Year" is abbreviated as "YR") and designated MN211.

The resulting seed of MN211, designated N211 was planted in a plot 3756 in YR2. Three plants were selected based on having branches on branches on branches.

The seed (4247) from one of the plants was planted in a plot 1761 in YR3. Two individual plants were selected based on being very good individual plants that were better than the parents.

The seed (6644) from one of the plants was planted in a plot 1732 in YR4. Six individual plants were selected based having weather shatter resistance and being equal to sister plots with a high yield.

The designator was changed to X26M. The seed (3846) from one of the plants was planted in a plot 0616 in YR5. Five individual plants were selected based on having a high yield and looking like S26 with improved non-dehiscence shatter resistance and a yield sample was taken.

The seed (Y023) from the yield sample was planted in a plot 3737 in YR6. Two individual plants were selected based on having a high yield and improved non-dehiscence and longer capsule zones than S26.

The seed (0965) from one of the plants was planted in a plot 7103 in YR7. Five individual plants were selected based on surviving a bad part of the field.

The seed (2314) from one of the plants was planted in a plot WB47 in YR8. A bulk of 114 plants was selected based on having a high yield and being uniform.

The seed (0721) from the plants was planted in strip plot W345 in YR8-9 in a winter nursery. The plot was rogued and all of the plants were harvested based on ability to do very well in low moisture compared to the other lines under the same conditions.

The seed (26MCR) from the plants was planted in plot 1424 in YR10. A bulk of 92 plants was harvested based on a good yield and profuse branching in a very wide row.

The seed (1424) from the plants was planted in test strip XE33 in YR11. The whole strip was harvested.

The seed (26MGW) from the strip was planted in a farmer field in YR12 for final verification of weather shatter resistance, lodging tolerance, combinability, and yield. The line was uniform and repeated on having good weather shatter resistance and excellent lodging tolerance. Part of the strip was harvested for an increase and part was left for a combine test. The line combined well with no issues. The designator was changed to Sesaco 38. The variety was released to farmers in YR13.

Along with breeding programs for sesame, tissue culture of sesame is currently being practiced in such areas of the world as Korea, Japan, China, India, Sri Lanka and the United States. One of ordinary skill in the art may utilize sesame plants grown from tissue culture as parental lines in the production of non-dehiscent sesame. Further IND sesame may be propagated through tissue culture methods. By means well known in the art, sesame plants can be regenerated from tissue culture having all the physiological and morphological characteristics of the source plant.

The present invention includes the seed of sesame variety S38 deposited on Mar. 13, 2014 with the American Type Culture Collection (ATCC) Patent Depository under ATCC Accession No. PTA-121090; a sesame plant or parts thereof produced by growing the seed deposited under ATCC Accession No. PTA-121090; any sesame plant having all the physiological and morphological characteristics of sesame variety S38; any sesame plant having all the physiological and morphological characteristics of a sesame plant produced by growing the seed deposited under ATCC Accession No. PTA-121090. The present invention also includes a tissue culture of regenerable cells produced from the seed having been deposited under ATCC Accession No. PTA-121090 or a tissue culture of regenerable cells from sesame variety S38 or a part thereof produced by growing the seed of sesame variety S38 having been deposited under ATCC Accession No. PTA-121090. A sesame plant regenerated from a tissue culture of regenerable cells produced from the seed having been deposited under ATCC Accession No. PTA-121090 or from sesame variety S38, wherein the regenerated sesame plant has all the physiological and morphological characteristics of sesame variety S38 is also contemplated by the present invention. Methods of producing sesame seed, comprising crossing a first parent sesame plant with a second parent sesame plant, wherein the first or second parent sesame plant was produced by seed having been deposited under ATCC Patent Deposit Designation No. PTA-121090 is part of the present invention.

Unless otherwise stated, as used herein, the term plant includes plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like. Further, unless otherwise stated, as used herein, the term progeny includes plants derived from plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like.

Sesame cultivar S38 has been tested experimentally over several years under various growing conditions ranging from South Texas to Southern Oklahoma. Sesame cultivar S38 has shown uniformity and stability within the limits of environmental influence for the characters listed in Table II below. Table II provides the name, definition, and rating scale of each character as well as the method by which the character is measured. Under the rating section, the rating for S38 is presented in bold text. Additionally, the distribution of the character in Sesaco's sesame development program is indicated under the rating section. Sesaco uses slightly different character specifications from "Descriptors for sesame", AGP: IBPGR/80/71, IBPGR Secretariat, Rome, (1981) and from the form "Sesame (*Sesamum indicum*)", U.S. Department of Agriculture Plant Variety Protection Office, Beltsville, Md. The descriptors in those documents were developed in the early 1980s and have not been updated to incorporate new concepts in sesame data collection.

Table II provides characteristics of S38 for forty-five (45) traits. Numerical ratings and values reported in this table were experimentally determined for S38 with prior sesame varieties in side by side replicated trials. Actual numerical values and ratings for a given variety will vary according to the environment, and the values and ratings provided in Table II were obtained in the environment specified in the parenthetical following the S38 rating. If "NT" is indicated, it indicates that trait was not tested. Table V provides a direct comparison between the new S38 variety and the prior varieties thus demonstrating the relative differences between the varieties in the side by side trials.

TABLE II

Characters Distinguishing the S38 Line

| Character | Rating | Methodology |
| --- | --- | --- |
| (1) BRANCHING STYLE<br>The potential amount of true branching in a line | S38 = B<br>(All crops, all nurseries)<br>Subjective rating based on the following values:<br>U = Uniculm - no branching except weak branches in open<br>B = True branches<br>Distribution within Sesaco based on stable lines in the crossing program in 1982-2001 (Total number of samples tested = 1,333)<br>U = 42.4%<br>B = 57.6% | The amount of branching on any particular plant depends on the space around the plant. In high populations, branching can be suppressed. This rating should be based on potential as expressed on end plants and plants in the open. True branches start in the leaf axil below the first flower, and they begin to emerge before the first open flower. As long as there is light into the leaf axils, there will be additional branches that start below the first branches in subsequently lower nodes. Weak branches occur when a plant is in the open. They develop in the lowest nodes and subsequent branches start at higher nodes. There are lines that will not branch in any circumstance. Some lines in the open will put on spontaneous branches late in the cycle. True and weak branches do not have a capsule in the same leaf axil, whereas the spontaneous branches form under the capsule after the capsule has formed. Spontaneous branches are not counted as branches.<br>There are rare lines where the flowering pattern is to put on flowers on lower nodes late in the cycle. In this case, the capsule is formed after the branch is developed. This pattern should not be termed spontaneous branching, and the branch is normally counted as a true branch.<br>There are branched lines that have secondary branches on the branches. In a few cases, there can be tertiary branches. Additional branches generally appear in low populations.<br>COMMENTS: the effects of light appear to have more of an effect on branching than moisture and fertility. High populations suppress branching. |
| (2) NUMBER OF CAPSULES PER LEAF AXIL<br>The predominant number of capsules per leaf axil in the middle half of the capsule zone | S38 = 1<br>(All crops, all nurseries)<br>Subjective rating based on the following values:<br>1 = Single<br>3 = Triple<br>Based on potential as described in the methodology presented herein<br>Distribution within Sesaco based on stable lines in the crossing program in 1982-2001 (Total number of samples tested = 1,327)<br>1 = 58.3%<br>3 = 41.7% | Rating can be taken from about 60 days after planting through to the end of the crop.<br>NUMBER OF CAPSULES PER LEAF AXIL is highly dependent on moisture, fertility, and light. In triple capsule lines, the central capsule forms first, and axillary capsules follow a few days later. Triple capsule lines have the potential to put on axillaries, but will not do so if plants do not have adequate moisture and/or fertility. In drought conditions, some triple capsule lines will produce only a central capsule for many nodes. In these lines, when there is adequate moisture through rain or irrigation, some will add axillary capsules on only new nodes, while others will add axillary capsules to all nodes. Some triple capsule lines will not put on axillary capsules if there is no direct sunlight on the leaf axil. To date, lines with single capsules have nectaries next to the central capsule in the middle of the capsule zone while triple capsules do not. However, some lines have what appear to be nectaries on the lower capsules of triple lines, but upon close examination, they are buds, which may or may not eventually develop into a flower and then a capsule. In |

TABLE II-continued

Characters Distinguishing the S38 Line

| Character | Rating | Methodology |
|---|---|---|
| | | most triple capsule lines, the lower and upper nodes have single capsules. There are some lines where the end plants can put on 5 capsules/leaf axil and a few that have the potential to put on 7 capsules/leaf axil. 5 and 7 capsules only appear with open plants with high moisture and fertility. In some environments, single capsule lines will put on multiple capsules on 1 node and rarely on up to 5 nodes. These lines are not considered triple capsule lines. |
| (3) MATURITY CLASS The maturity of a line in relation to a standard line. Currently, the standard line is S26 at 100 days | S38 = M for 103 days (Uvalde nursery[a], 2008-2011) Subjective rating based on the following values: V = Very early (<85 days) E = Early (85-94 days) M = Medium (95-104 days) L = Late (105-114 days) T = Very late (>114 days) Distribution within Sesaco based on stable lines in the crossing program in 1998-2001 (Total number of samples tested = 650) V = 1.2% E = 26.8% M = 56.2% L = 12.9% T = 2.9% | The basis for this data point is DAYS TO PHYSIOLOGICAL MATURITY (Character No. 29). S26 is the standard line to be used to compute MATURITY CLASS. For each line, the physiological maturity for each year is subtracted by the S26 maturity for that year in that nursery, and then the number of days of difference is averaged. The average is then added to 100. See DAYS TO PHYSIOLOGICAL MATURITY (Character No. 29) for the effects of the environment on MATURITY CLASS. Note that S24 was formerly used as the standard for this trait. S26 averages approximately 5 days longer than S24. |
| (4) PLANT PHENOTYPE A three character designation that provides the branching style, number of capsules per leaf axil, and the maturity class | S38 = B1M (All crops; all nurseries) Subjective rating based on the following values: BRANCHING STYLE U = Uniculm - no branching except weak branches in open B = True branches NUMBER OF CAPSULES PER LEAF AXIL 1 = Single 3 = Triple MATURITY CLASS V = Very early (<85 days) E = Early (85-94 days) M = Medium (95-104 days) L = Late (105-114 days) T = Very late (>114 days) Distribution within Sesaco based on stable lines in the crossing program in 1998-2001 (Total number of samples tested = 650) U1V = 0%   U3V = 1.1% U1E = 3.8%   U3E = 8.3% U1M = 16.0%   U3M = 12.0% U1L = 3.4%   U3L = 2.2% U1T = 0.5%   U3T = 0.6% B1V = 0%   B3V = 0.2% B1E = 8.0%   B3E = 6.3% B1M = 23.2%   B3M = 4.8% B1L = 6.5%   B3L = 1.0% B1T = 1.6%   B3T = 0.4% | The first character is the BRANCHING STYLE (Character No. 1), followed by the NUMBER OF CAPSULES PER LEAF AXIL (Character No. 2), and then the MATURITY CLASS (Character No. 3). When these characters are placed in a matrix, there are 20 potential phenotypes. The phenotype provides an overview of the general appearance of the plant. There is a very high correlation between MATURITY CLASS and HEIGHT OF PLANT (Character No. 5). |
| (5) HEIGHT OF PLANT The height of the plant from the ground to the top of the highest capsule with viable seed | S38 = 126 cm (Uvalde nursery, 2013) Value based on the average of a minimum of three plants (unit of measure: cm) Distribution within Sesaco based on stable lines in the crossing program in | The measurement is made after the plants stop flowering. For plants that are not erect or have lodged, the plant should be picked up for the measurement. In most lines the highest capsule is on the main stem. In lines with the dt/dt alleles (determinate), the highest capsule is on the branches. COMMENTS: this height is dependent |

TABLE II-continued

Characters Distinguishing the S38 Line

| Character | Rating | Methodology |
|---|---|---|
| | 1999-2001 (Total number of samples tested = 2,274) low = 56 cm; high = 249 cm<br>1 = <94.6 cm; 5.2%<br>2 = <133.2 cm; 34.6%<br>3 = <171.8 cm; 54.9%<br>4 = <210.4 cm; 5.1%<br>5 = >210.3 cm; 0.1%<br>avg. = 134.8 cm, std = 23.5 | on the amount of moisture, heat, fertility, and population. Increased values generally increase the height. In a high population, the height will only increase if there is adequate fertility and moisture; otherwise, the height will be shorter. In low light intensities, the heights are generally taller. |
| (6) HEIGHT OF FIRST CAPSULE<br>The height of the first capsule from the ground to the bottom of the lowest capsule on the main stem | S38 = 69 cm (Uvalde nursery, 2013) Value based on the average of a minimum of three plants (unit of measure: cm) Distribution within Sesaco based on stable lines in the crossing program in 1999-2001 (Total number of samples tested = 2,274) low = 20 cm; high = 193 cm<br>1 = <54.6 cm; 52.7%<br>2 = <89.2 cm; 45.5%<br>3 = <123.8 cm; 1.5%<br>4 = <158.4 cm; 0.3%<br>5 = >158.3 cm; 0.1%<br>avg. = 54.2 cm, std =14.3 | The measurement is made after the plants stop flowering. For plants that are not erect or have lodged, the plant should be picked up for the measurement. In most lines, the lowest capsule is on the main stem. True branches have capsules higher than on the main stem except when the flowers fall off the main stem. Occasionally, on weak branches, the lowest capsule is on the branches. There are lines that flower in the lower nodes late in the cycle, and, thus, the measurement should be taken after flowering ends. In many lines the first flower does not make a capsule, and, thus, this height may not be the same as the height of the first flower. The height is correlated to the length of time to flowering, the earlier the lower the height. COMMENTS: see HEIGHT OF PLANT (Character No. 5) for effects of environmental factors |
| (7) CAPSULE ZONE LENGTH<br>The length of the capsule zone. The capsule zone extends from the bottom of the lowest capsule on the main stem to the top of the highest capsule on the main stem. | S38 = 57 cm (Uvalde nursery, 2013) Value based on the average of a minimum of three plants (unit of measure: cm) Distribution within Sesaco based on stable lines in the crossing program in 1999-2001 (Total number of samples tested = 2,274) low = 18 cm; high = 188 cm<br>1 = <52 cm; 4.7%<br>2 = <86 cm; 53.5%<br>3 = <120 cm; 41.3%<br>4 = <154 cm; 0.5%<br>5 = >153.9 cm; 0.1%<br>avg. = 80.6 cm, std = 17.2 | The measurement is derived by subtracting the HEIGHT OF FIRST CAPSULE (Character No. 6) from the HEIGHT OF PLANT (Character No. 5). COMMENTS: see HEIGHT OF PLANT (Character No. 5) for effects of environmental factors |
| (8) NUMBER OF CAPSULE NODE PAIRS<br>The number of capsule node pairs from the lowest capsule node to the highest node with capsules with viable seed on the main stem of the plant | S38 = 32 pairs (Uvalde nursery, 2013) Value based on the average of a minimum of three plants (unit of measure: number) Distribution within Sesaco based on stable lines in the crossing program in 1999-2001 (Total number of samples tested = 2,154) low = 10; high = 54<br>1 = <18.8; 17.9%<br>2 = <27.6; 48.3%<br>3 = <36.4; 29.5%<br>4 = <45.2; 3.6%<br>5 = >45.1; 0.7%<br>avg. = 25.3, std = 6.4 | The count is made after the plants stop flowering. On opposite and alternate arranged leaves, each pair of leaves is counted as one node pair. In some lines, there are three leaves per node for at least part of the plant, and those are counted as one node pair. In some plants, flowers may not have produced capsules on one or more of the leaf axils in a node. These node pairs should still be counted. Node pairs on the branches are not counted. In years when the amount of moisture available to the plant is irregular, node pairs can become very irregular, particularly on triple capsule lines. In the upper portions of the plant, it may become easier to count the capsule clusters and divide by 2. While it is possible to count node pairs after leaves have fallen, it is much easier to count while the leaves are still on the plant. |

TABLE II-continued

Characters Distinguishing the S38 Line

| Character | Rating | Methodology |
|---|---|---|
| | | COMMENTS: the number of node pairs is dependent on the amount of moisture and fertility. Higher moisture and fertility increases the number of node pairs. |
| (9) AVERAGE INTERNODE LENGTH WITHIN CAPSULE ZONE<br>The average internode length within the capsule zone | S38 = 1.7 cm (Uvalde nursery, 2013)<br>Value based on the average of a minimum of three plants (unit of measure: cm)<br>Distribution within Sesaco based on stable lines in the crossing program in 1999-2001 (Total number of samples tested = 2,145)<br>low = 1.09 cm; high = 8.09 cm<br>1 = <2.49 cm; 6.2%<br>2 = <3.89 cm; 74.6%<br>3 = <5.29 cm; 18.6%<br>4 = <6.69 cm; 0.4%<br>5 = >6.68 cm; 0.1%<br>avg. = 3.35 cm, std = 0.66 | Divide the CAPSULE ZONE LENGTH (Character No. 7) by the NUMBER OF CAPSULE NODES (Character No. 8).<br>COMMENTS: this length is dependent on the amount of moisture, fertility, and population. Increased values generally increase the length. In a high population, the length will only increase if there is adequate fertility and moisture; otherwise the length will be shorter. In low light intensities, the lengths are generally longer.<br>Past methodologies have measured the internode length at the middle of the capsule zone. Some have measured it at the median node and others at the median CAPSULE ZONE LENGTH. |
| (10) YIELD AT DRYDOWN<br>An extrapolation of the yield of a field by taking sample yields | S38 = 1,487 kg/ha (Uvalde nursery, 2013)<br>1,388 kg/ha (Rio Hondo nursery[b], 2013)<br>Values based on the average of a minimum of three replications (unit of measure: kg/ha)<br>Distribution within Sesaco based on stable lines in the crossing program in 1999-2001 (Total number of samples tested = 1,828)<br>low = 67 kg/ha<br>high = 2421 kg/ha<br>1 = <537.8 kg/ha; 5.6%<br>2 = <1008.6 kg/ha; 15.6%<br>3 = <1479.4 kg/ha; 51.5%<br>4 = <1950.2 kg/ha; 25.8%<br>5 = >1950.1 kg/ha; 1.4%<br>avg. = 1114.6 kg/ha, std = 331.2 | On 3 replicated plots, when the plants are dry enough for direct harvest, cut a minimum of 1/5000 of a hectare (Sesaco uses 1/2620) in the plot and place the plants in a cloth bag. Thresh the sample in a plot thresher and weigh the seed. Multiply the weight by the appropriate multiplier based on area taken to provide the extrapolated yield in kg/ha.<br>In the Almaco thresher there is about 3% trash left in the seed. Since yields are comparative, there is no cleaning of the seed done before the computation. If other threshers have more trash, the seed should be cleaned before weighing.<br>COMMENTS: yields increase with moisture and fertility. However, too high a moisture can lead to killing of plants. Too high fertility can lead to extra vegetative growth that may not lead to higher yields. The optimum population depends on the PLANT PHENOTYPE, Character No. 4 (BRANCHING STYLE, Character No. 1; NUMBER OF CAPSULES PER LEAF AXIL, Character No. 2; and MATURITY CLASS, Character No. 3) and row width. |
| (11) TOLERANCE TO DROUGHT<br>The relative amount of tolerance to drought | S38 = NT<br>Average of a minimum of three plots of a subjective rating based on the following values:<br>0 to 8 scale<br>7 = Little effect from drought<br>4 = Medium effect from drought<br>1 = Considerable effect from drought<br>Intermediate values are used.<br>Distribution within Sesaco based on stable lines in the crossing program in 2000 (Total number of samples tested = 632)<br>low = 0; high = 8<br>1 = <1.6; 0.8%<br>2 = <3.2; 28.0%<br>3 = <4.8; 36.1%<br>4 = <6.4; 34.5%<br>5 = >6.3; 0.6%<br>avg. = 4.1, std = 1.2 | In a year when there is a drought; this rating can be used to differentiate the effects of the different lines. This is a subjective rating requiring a rater that is familiar with the performance of the line under normal conditions. The rating is based on how the drought changes the line from normal. Thus, a short line that does not change significantly in a drought may have a higher rating than a tall line, which is affected by the drought even though the taller line is taller in the drought than the short line. |

TABLE II-continued

Characters Distinguishing the S38 Line

| Character | Rating | Methodology |
|---|---|---|
| (12) LEAF LENGTH The length of the leaf blade from the base of the petiole to the apex of the leaf from the $5^{th}$, $10^{th}$, and $15^{th}$ node pairs | S38 = NT Value based on the average of a minimum of three plants (unit of measure: cm) Distribution within Sesaco for $5^{th}$ leaf based on stable lines in the crossing program in 2002 (Total number of lines tested = 196 with 711 samples) low = 13.8 cm; high = 42.5 cm 1 = <19.5 cm; 34.7% 2 = <25.3 cm; 48.0% 3 = <31.0 cm; 14.3% 4 = <36.8 cm; 1.5% 5 = >36.7 cm; 1.5% avg. = 21.5 cm, std = 4.4 Distribution within Sesaco for $10^{th}$ leaf based on stable lines in the crossing program in 2002 (Total number of lines tested = 196 with 711 samples) low = 9.3 cm; high = 32.9 cm 1 = <14.0 cm; 22.4% 2 = <18.7 cm; 41.8% 3 = <23.5 cm; 20.9% 4 = <28.2 cm; 10.2% 5 = >28.1 cm; 4.6% avg. = 17.9 cm, std = 4.8 Distribution within Sesaco for $15^{th}$ leaf based on stable lines in the crossing program in 2002 (Total number of lines tested = 196 with 711 samples) low = 4.4 cm; high = 26.2 cm 1 = <8.8 cm; 5.1% 2 = <13.1 cm; 42.9% 3 = <17.5 cm; 29.8% 4 = <21.8 cm; 15.8% 5 = >21.7 cm; 6.6% avg. = 14.3 cm, std = 4.2 | Select one leaf per node to measure from the $5^{th}$, $10^{th}$, and $15^{th}$ node pairs from the base of the plant. All the leaves for one line should be collected at the same time. Some lines retain the cotyledons, and the cotyledon node does not count as a node pair. In some lines the lowest leaves abscise leaving a scar on the stem. Abscised nodes should be counted. In lines with alternate leaves, one node is counted for each pair of leaves. In some lines in parts of the plant there are three leaves per node, which should be counted as one node. The leaves continue growing in the first few days after they have separated from the growing tip. The choosing of leaves should be done a minimum of 5 days after the $15^{th}$ node has appeared. Timing is important, because the plants will begin to shed their lower leaves towards the end of their cycle. There are lines that have less than 15 nodes. In this case, the highest node should be taken and the node number annotated to the measurements. There can be as much as 6 mm difference between a green leaf and a dry leaf. The measurements can be done on a green or dry leaf as long as any comparison data with other lines is based on the same method. Generally, the lowest leaves increase in size until the $4^{th}$ to $6^{th}$ node and then they decrease in size. This applies to LEAF LENGTH (Character No. 12), LEAF BLADE WIDTH (Character No. 14), and PETIOLE LENGTH (Character No. 15). In few cases, LEAF BLADE LENGTH Character No. 13) can increase up the $10^{th}$ node, but will decrease by the $15^{th}$ node. Generally, the width will decrease at a greater rate than the length. COMMENTS: the length is dependent on the amount of moisture and fertility. Higher moisture and fertility increase the length. Leaf size also appears to be affected by light intensity. In Korea, the Korean lines have much larger leaves than in Oklahoma. In Korea, there is more cloud cover and a general haze than in Oklahoma. |
| (13) LEAF BLADE LENGTH The length of the leaf blade from the base of the leaf blade to the apex of the leaf from the $5^{th}$, $10^{th}$, and $15^{th}$ node pairs | S38 = NT Value based on the average of a minimum of three plants (unit of measure: cm) Distribution within Sesaco for $5^{th}$ leaf based on stable lines in the crossing program in 2002 (Total number of lines tested = 196 with 711 samples) low = 9.0 cm; high = 25.5 cm 1 = <12.3 cm; 14.3% 2 = <15.6 cm; 60.2% 3 = <18.9 cm; 20.9% 4 = <22.2 cm; 3.1% 5 = >22.1 cm; 1.5% avg. = 14.4 cm, std = 2.4 Distribution within Sesaco for $10^{th}$ leaf based on stable lines in the crossing program in 2002 (Total number of lines tested = | See LEAF LENGTH (Character No. 12) on how to collect leaves. The measurement does not include PETIOLE LENGTH (Character No. 15). In some leaves the blade on one side of the petiole starts before the other side. This measure should start from the lowest blade side. There are leaves that have enations where a blade starts and then stops. The enations are not considered part of the leaf blade because they are very irregular from plant to plant and within a plant. COMMENTS: see LEAF LENGTH (Character No. 12) for effects of environment |

TABLE II-continued

Characters Distinguishing the S38 Line

| Character | Rating | Methodology |
|---|---|---|
| | 196 with 711 samples) low = 8.3 cm; high = 23.4 cm<br>1 = <11.3 cm; 18.9%<br>2 = <14.3 cm; 42.9%<br>3 = <17.4 cm; 25.0%<br>4 = <20.4 cm; 9.2%<br>5 = >20.3 cm; 4.1%<br>avg. = 13.9 cm, std = 3.0<br>Distribution within Sesaco for 15$^{th}$ leaf based on stable lines in the crossing program in 2002 (Total number of lines tested = 196 with 711 samples) low = 4.2 cm; high = 20.7 cm<br>1 = <7.5 cm; 2.0%<br>2 = <10.8 cm; 36.7%<br>3 = <14.1 cm; 37.8%<br>4 = <17.4 cm; 16.3%<br>5 = >17.3 cm; 7.1%<br>avg. = 12.0 cm, std = 3.0 | |
| (14) LEAF BLADE WIDTH<br>The width of the leaf blade measured across the leaf blade at the widest point at the 5$^{th}$, 10$^{th}$, and 15$^{th}$ node pairs | S38 = NT<br>Value based on the average of a minimum of three plants (unit of measure: cm)<br>Distribution within Sesaco for 5$^{th}$ leaf based on stable lines in the crossing program in 2002 (Total number of lines tested = 196 with 711 samples) low = 3.4 cm; high = 31.0 cm<br>1 = <8.9 cm; 53.1%<br>2 = <14.4 cm; 33.7%<br>3 = <20.0 cm; 9.7%<br>4 = <25.5 cm; 2.6%<br>5 = >25.4 cm; 1.0%<br>avg. = 9.6 cm, std = 4.3<br>Distribution within Sesaco for 10$^{th}$ leaf based on stable lines in the crossing program in 2002 (Total number of lines tested = 196 with 711 samples) low = 1.3 cm; high = 17.6 cm<br>1 = <4.6 cm; 69.4%<br>2 = <7.8 cm; 25.0%<br>3 = <11.1 cm; 4.6%<br>4 = <14.3 cm; 0%<br>5 = >14.2 cm; 1.0%<br>avg. = 4.3 cm, std = 2.2<br>Distribution within Sesaco for 15$^{th}$ leaf based on stable lines in the crossing program in 2002 (Total number of lines tested = 196 with 711 samples) low = 0.7 cm; high = 6.0 cm<br>1 = <1.8 cm; 29.1%<br>2 = <2.8 cm; 48.0%<br>3 = <3.9 cm; 15.3%<br>4 = <4.9 cm; 4.6%<br>5 = >4.8 cm; 3.1%<br>avg. = 2.3 cm, std = 0.9 | See LEAF LENGTH (Character No. 12) on how to collect leaves. There are many leaves that are not symmetrical with lobing on one side and not the other. The width should still be measured across the widest point on a line perpendicular to the main vein of the leaf.<br>On some lines the width exceeds the length, particularly on lobed leaves.<br>COMMENTS: see LEAF LENGTH (Character No. 12) for effects of environment<br>The widest leaves are lobed. Normally, the leaves have turned from lobed to lanceolate by the 10$^{th}$ leaf with the exception of the tropical lines. |
| (15) PETIOLE LENGTH<br>The length of the petiole from the base of the petiole to the start of the leaf blade at the | S38 = NT<br>Value based on the average of a minimum of three plants (unit of measure: cm) | See LEAF BLADE LENGTH (Character No. 13) on how to collect leaves. In some leaves, the blade on one side of the petiole starts before the other side. This measure should end where the earliest blade starts. |

TABLE II-continued

Characters Distinguishing the S38 Line

| Character | Rating | Methodology |
|---|---|---|
| $5^{th}$, $10^{th}$, and $15^{th}$ node pairs | Distribution within Sesaco for $5^{th}$ leaf based on stable lines in the crossing program in 2002 (Total number of lines tested = 196 with 711 samples) low = 3.0 cm; high = 17.0 cm<br>1 = <5.8 cm; 35.2%<br>2 = <8.6 cm; 39.8%<br>3 = <11.4 cm; 19.4%<br>4 = <14.2 cm; 4.1%<br>5 = >14.1 cm; 1.5%<br>avg. = 7.0 cm, std = 2.5<br>Distribution within Sesaco for $10^{th}$ leaf based on stable lines in the crossing program in 2002 (Total number of lines tested = 196 with 711 samples) low = 1.0 cm; high = 14.2 cm<br>1 = <3.6 cm; 53.6%<br>2 = <6.3 cm; 31.6%<br>3 = <8.9 cm; 11.7%<br>4 = <11.6 cm; 2.0%<br>5 = >11.5 cm; 1.0%<br>avg. = 4.0 cm; std = 2.1<br>Distribution within Sesaco for $15^{th}$ leaf based on stable lines in the crossing program in 2002 (Total number of lines tested = 196 with 711 samples) low = 0.2 cm; high = 7.4 cm<br>1 = <1.6 cm; 38.8%<br>2 = <3.1 cm; 41.8%<br>3 = <4.5 cm; 13.3%<br>4 = <6.0 cm; 3.1%<br>5 = >5.9 cm; 3.1%<br>avg. = 2.3 cm, std = 1.3 | There are leaves that have enations where a blade starts and then stops. The enations are not considered part of the leaf blade because they are very irregular from plant to plant and within a plant and should be measured as part of the petiole.<br>COMMENTS: see LEAF LENGTH (Character No. 12) for effects of environment |
| (16) NUMBER OF CARPELS PER CAPSULE<br>The predominant number of carpels per capsule in the middle half of the capsule zone | S38 = 2<br>(All crops, all nurseries)<br>Subjective rating based on the following values:<br>2 = bicarpellate<br>3 = tricarpellate<br>4 = quadricarpellate<br>(unit of measure: actual number)<br>Distribution within Sesaco based on the introductions received in 1982-2001 (Total number of samples tested = 2702)<br>2 = 97.6%<br>3 = 0.0004%<br>4 = 2.3%<br>Sesaco has not developed lines with more than 2 carpels. | The rating can be taken from about 60 days after planting to all the way to the end of the crop.<br>There are many plants with mixed number of carpels as follows:<br>1. Some bicarpellate plants will have one or more nodes near the center of the capsule zone that have tri- and/or quadricarpellate capsules and vice versa.<br>2. Most tri- and quadri-carpellate plants will begin and end with bicarpellate nodes.<br>3. Some plants have only one carpel that develops. These capsules are generally bent, but on examination the $2^{nd}$ carpel can be seen.<br>4. On all types, flowers may coalesce and double or triple the number of carpels.<br>5. On the seamless gene plants (gs/gs) the false membranes do not form locules. These are still considered bicarpellate. |
| (17) CAPSULE LENGTH FROM 10cap TEST<br>The length of the capsule from the bottom of the seed chamber to the top of the seed chamber from the outside of the capsule. The tip of the capsule is not included in the measurement. | S38 = 2.31 cm<br>(All experimental nurseries, 1997-2011)<br>Value based on the average of a minimum of three samples of the length taken on the median capsule in a 10 capsule sample (unit of measure: cm)<br>Distribution within Sesaco based on 10cap test in all nurseries in 1997-2002 | After the plants are physiologically mature, take 2 capsules from five plants from the middle of the capsule zone. On three capsule per leaf axil lines, one central capsule and one axillary capsule should be taken from the same leaf axil. The measurement is taken on the median capsule of single capsule lines and on the median central capsule on three capsule lines. The measurement is taken on dry capsules because the length can shorten as much as one mm on drydown.<br>The 10 capsules can be sampled from |

TABLE II-continued

Characters Distinguishing the S38 Line

| Character | Rating | Methodology |
|---|---|---|
| | (Total number of lines tested = 1,613 with 8,285 samples)<br>low = 1.3 cm; high = 4.5 cm<br>1 = <1.94cm; 2.7%<br>2 = <2.58cm; 67.9%<br>3 = <3.22 cm; 27.2%<br>4 = <3.86 cm; 1.9%<br>5 = >3.85 cm; 0.3%<br>avg. = 2.44 cm, std = 0.33 | physiological maturity through complete drydown without an effect on this character.<br>Generally, the capsules in the middle of the capsule zone are the longest on the plant.<br>COMMENTS: the length of the capsule is dependent on the amount of moisture, fertility, and population. Higher moisture and fertility increase the length. Higher population decreases the length even with adequate moisture/fertility. |
| (18) SEED WEIGHT PER CAPSULE FROM 10cap TEST<br>The weight of the seed in a capsule from the center of the capsule zone | S38 = 0.244 g<br>(All experimental nurseries, 1997-2011)<br>Value based on the average of a minimum of three samples of the weight of 10 capsules (unit of weight: grams)<br>Distribution within Sesaco based on 10cap test in all nurseries in 1997-2002<br>(Total number of lines tested = 1,613 with 8,285 samples)<br>low = 0.053 g; high = 0.476 g<br>1 = <0.138 g; 1.3%<br>2 = <0.222 g; 47.6%<br>3 = <0.307 g; 50.6%<br>4 = <0.391 g; 1.1%<br>5 = >0.390 g; 0.1%<br>avg. = 0.221 g, std = 0.039 | See CAPSULE LENGTH FROM 10CAP TEST (Character No. 17) for collection of capsules. The capsules should be dried, the seed threshed out, and the seed weighed.<br>The 10 capsules can be sampled from physiological maturity through complete drydown without an effect on this character. After drydown, only capsules with all their seed are taken. Thus, this test cannot be done on shattering lines after drydown.<br>Generally, the capsules in the middle of the capsule zone have the highest seed weight per capsule on the plant.<br>COMMENTS: see CAPSULE LENGTH FROM 10CAP TEST (Character No. 17) for the effects of environmental factors. |
| (19) CAPSULE WEIGHT PER CAPSULE FROM 10cap TEST<br>The weight of the capsule from the center of the capsule zone after the seed has been removed | S38 = 0.167 g<br>(All experimental nurseries, 1997-2011)<br>Value based on the average of a minimum of three samples of the weight of 10 capsules (unit of measure: grams)<br>Distribution within Sesaco based on 10cap test in all nurseries in 1997-2002<br>(Total number of lines tested = 1,613 with 8,285 samples)<br>low = 0.059 g; high = 0.395 g<br>1 = <0.126 g; 22.6%<br>2 = <0.193 g; 69.1%<br>3 = <0.261 g; 8.2%<br>4 = <0.328 g; 0.9%<br>5 = >0.327 g; 0.6%<br>avg. = 0.152 g, std = 0.036 | See CAPSULE LENGTH FROM 10CAP TEST (Character No. 17) for collection of capsules. The capsules should be dried, the seed threshed out, and the capsules weighed. At times the peduncle can still be attached to the capsules. The peduncles should be removed and not weighed.<br>The 10 capsules can be sampled from physiological maturity through complete drydown without an effect on this character.<br>Generally, the capsules in the middle of the capsule zone have the highest capsule weight per capsule on the plant.<br>COMMENTS: see CAPSULE LENGTH FROM 10CAP TEST (Character No. 17) for the effects of environmental factors. |
| (20) CAPSULE WEIGHT PER CM OF CAPSULE<br>The weight of a capsule per cm of capsule from the center of the capsule zone | S38 = 0.072 g<br>(All experimental nurseries, 1997-2011)<br>Value based on the average of a minimum of three samples of the weight per cm of 10 capsules (unit of measure: grams)<br>Distribution within Sesaco based on 10cap test in all nurseries in 1997-2002<br>(Total number of lines tested = 1,613 with 8,285 samples)<br>low = 0.027 g; high = 0.123 g<br>1 = <0.046 g; 8.2%<br>2 = <0.065 g; 55.5%<br>3 = <0.085 g; 36.5 | The weight is derived by dividing the CAPSULE WEIGHT PER CAPSULE FROM 10CAP TEST (Character No. 19) by the CAPSULE LENGTH FROM 10CAP TEST (Character No. 17).<br>The 10 capsules can be sampled from physiological maturity through complete drydown without an effect on this character.<br>COMMENTS: this character is used instead of capsule width. Capsule width is difficult to measure because there are so many variables in a capsule. In a bicarpellate capsule, the width differs when measuring across one carpel or both carpels. Capsules can also vary through the length of the capsule by being substantially narrower at the bottom, middle or top of the capsule. In 1997, four widths were measured on each capsule |

TABLE II-continued

Characters Distinguishing the S38 Line

| Character | Rating | Methodology |
|---|---|---|
| | 4 = <0.104 g; 4.4%<br>5 = >0.103 g; 0.5%<br>avg. = 0.063 g; std = 0.012 | and then averaged. This average had a very high correlation to the capsule weight per cm of capsule.<br>See CAPSULE LENGTH FROM 10CAP TEST (Character No. 17) for effects of environmental factors |
| (21) VISUAL SEED RETENTION<br>Amount of seed in most of the capsules in the middle half of the capsule zone when the plant(s) are dry enough for direct harvest with a combine | S38 = I<br>(All crops, all nurseries)<br>Subjective rating based on the following values:<br>X = <50% seed retention (unsuitable for direct harvest)<br>C = 50-74% seed retention (unsuitable for direct harvest, but may segregate V or above in future generations)<br>V = >74% seed retention (sufficient seed retention for 10cap testing)<br>W = >74% seed retention on weathering in field after rains and/or winds<br>I = in using the "drum test" the seed in the capsules do not rattle and >85% of the capsules on the plant(s) harvested have visible seed in the tips of the capsules four or more weeks after the ideal harvest time. The "I" rating is used for all of the capsules on the plant.<br>'+' and '−' modifiers can be used. | This rating is used for plants that are being selected for advanced testing whether individually or in a bulk with all the plants having the same level of seed retention.<br>Most "X" plants can be identified from the first capsule that dries since the seed will begin falling out immediately.<br>A "C" (close to V) plant will have some capsules with seed and some without.<br>A "V" (visual shatter resistance) plant can be identified when the first 50% of the capsules have dried, but a "V+" rating should not be used until the complete plant is dry and most of the capsules are showing seed retention.<br>Some "V" plants can be upgraded to "W" after the dry capsules have been subjected to weather (rain and/or wind)<br>"V" and "W" become non-dehiscent only after 10cap testing with about an 80% passing rate. 10cap testing is done on "I" selections have had about a 99% passing rate.<br>The "drum test" consists of placing the fingers from one hand about ½ inch from the center of the main stem and then striking the stem alternately with one finger and then the other finger in rapid succession. The human ear can perceive degree of rattling over a range. IND is defined as having no rattle. Degree of rattle in this test correlates with loss of increasing amounts of seed as capsules are exposed to weather conditions.<br>.<br>COMMENTS: the ratings above should be made under normal conditions (600 mm of annual rainfall and 30 kg/ha of nitrogen) through high moisture/fertility conditions. In drought or very low fertility conditions, it has been observed that there is less seed retention. In addition, high populations may lead to low moisture or fertility causing less seed retention. If unusual environmental conditions are present, the effects should be taken into consideration prior to rating. |
| (22) SHAKER SHATTER RESISTANCE FROM 10cap TEST<br>The amount of seed retention after the capsules are dry, inverted, and put through a shaker (10 capsule sample) | S38 = 81.8 %<br>(All experimental nurseries, 1997-2011)<br>Value based on the average of a minimum of three samples of the percentage of seed retained in 10 capsules (unit of measure: Actual Number expressed as percentage)<br>Distribution within Sesaco based on 10cap test in all nurseries in 1997-2002 (Total number of lines tested = 1,613 with 8,285 samples)<br>low = 0; high = 100<br>1 = <20; 12.9%<br>2 = <40; 6.9 % | See CAPSULE LENGTH FROM 10CAP TEST (Character No. 17) for collection of capsules. The capsules should be dried and inverted. The capsules and any seed that has fallen out should then be placed in flasks on a reciprocal shaker with a 3.8 cm stroke with 250 strokes/min for 10 minutes (see U.S. Pat. No. 6,100,452). The seed that comes out of the capsules should be weighed as 'out seed.' The retained seed should be threshed out of the capsules and weighed to compute the 'total seed'. The shaker shatter resistance is computed as a percentage as follows: (total seed − out seed)/total seed.<br>The 10 capsules can be sampled from physiological maturity through complete drydown without an effect on this character for shatter resistant types. When taking capsules after drydown, only capsules with |

TABLE II-continued

Characters Distinguishing the S38 Line

| Character | Rating | Methodology |
|---|---|---|
| | 3 = <60; 23.4%<br>4 = <80; 47.7%<br>5 = >79.9; 9.2%<br>avg. = 55.9%, std = 23.9 | all their seed are taken. Thus, this test cannot be done on shattering lines after drydown.<br>COMMENTS: The ratings above should be made under normal conditions through high moisture/fertility conditions. In drought or very low fertility conditions, it has been observed that there is less seed retention. In additions, high populations may lead to low moisture or fertility causing there to be less seed retention. If unusual environmental conditions are present, the effects should be taken into consideration prior to rating. Lines with shaker shatter resistance >64.9% are known as non-dehiscent lines (see U.S. Pat. No. 6,100,452). |
| (23) CAPSULE SHATTERING TYPE<br>Amount of seed retention in a line or plant | S38 = SR<br>(All crops, all nurseries)<br>Subjective rating based on the following values:<br>SUS = Super-shattering (<2 visual seed retention - equates to <25%)<br>SHA = Shattering (<4 visual seed retention - equates to <50%)<br>SSH = Semi-shattering (4-6 visual seed retention - equates to 50 to 75%)<br>SR = Shatter resistant (a numeric rating >6 visual seed retention without id or gs alleles - equates to >75%; an alphabetical rating of V, W, or I)<br>ID = Indehiscent (presence of id/id with capsule closed)<br>IDO = Indehiscent (presence of id/id with capsule open at tip)<br>GS = Seamless (presence of gs/gs with capsule closed)<br>GSO = Seamless (presence of gs/gs with capsule open at tip) | The rating is based on visual observations as to seed retention as the plants remain standing in the field without shocking.<br>GS plants can be identified while the plant is putting on capsules or at drydown because the carpels in the capsules do not form false membranes. There are plants that will have capsules with false membranes on the lower and upper nodes but most of the capsules show no false membranes.<br>ID plants can be identified during the growing season in that they have enations on the bottoms of the leaves. At drydown they are more difficult to distinguish from other lines that have closed capsules (other than GS). There is less of a suture than other capsule types.<br>SUS, SHA, SSH, and SR are defined by VISUAL SEED RETENTION (Character No. 21).<br>COMMENTS: Most environmental factors do not have much of an effect on capsule shattering type other than to make it more difficult to distinguish in the overlap zone. Generally, higher moisture, higher fertility, and lower populations will decrease the shattering a small amount - less than 10%.<br>The wind can have a large effect in decreasing the amount of seed retention. Rain, dew and fog can also reduce seed retention. |
| (24) NON-DEHISCENT TEST<br>A line that has passed the non-dehiscent test of having shaker shatter resistance >64.9% is considered an ND line in accordance with U.S. Pat. No. 6,100,452. | S38 = ND<br>(All crops, all nurseries)<br>Objective rating based on the following values:<br>ND = Non-dehiscent line<br>XX = Line that does not pass the non-dehiscent test<br>ND distribution within Sesaco based on 10cap test in all nurseries in 1997-2006<br>(Total number of samples tested = 10,905)<br>ND = 53.6%<br>XX = 46.4% | Lines are designated as ND only after they have undergone a minimum of 3 shaker shatter resistance tests. In order to be considered an ND variety, the line must pass the ND threshold in multiple nurseries for multiple years. |
| (25) IMPROVED NON-DEHISCENT VISUAL RATING<br>Amount of seed in most of the capsules in the plants in a plot four or more weeks after the ideal harvest time. | S38 = 7.33<br>(Uvalde nursery, 2011)<br>S38 = 7.22<br>(Lorenzo nursery[c], 2010)<br>Value based on the average of a minimum of three plots of a subjective rating based on the percentage of capsules | This rating is used for a plot or field that is being evaluated.<br>The data is taken four or more weeks after the ideal harvest time. See DAYS TO DIRECT HARVEST (Character No. 30). Estimate the percentage of capsules that have visible seed at the top. In the beginning in order to develop an eye for the rating, the evaluator should observe all |

TABLE II-continued

Characters Distinguishing the S38 Line

| Character | Rating | Methodology |
|---|---|---|
| | with visible seed retention<br>8 <100%<br>7 <85%<br>6 <70%<br>5 >55%<br>Z <55%<br>'*', '+', and '−' modifiers<br>can be used. For<br>averages, 0.5 is added for<br>a '*', 0.33 is added for a<br>'+', and 0.33 is subtracted<br>for a '−', e.g., "7+" = 7.33.<br>(Total number of lines<br>tested = 288 with 801<br>samples in 2006)<br>low = 2.97; high = 7.33<br>1 = <6.0; 2.1%<br>2 = <6.5; 20.8%<br>3 = <7.0; 13.2%<br>4 = <7.5; 63.9%<br>5 = >7.5; 0%<br>avg. = 6.77, std = 0.54<br>Note: The percentage of<br>lines between 7.0 and 7.6<br>is very high because<br>Sesaco has established a<br>new threshold for a new<br>variety of IND >6.9 and<br>only lines that are IND or<br>segregating IND are rated. | of the capsules and rate each of them; get<br>a count of those with visible seeds and a<br>count of total capsules; and compute a<br>percentage. Once the evaluator is skilled,<br>there is no need to count the capsules.<br>There is a very high correlation between<br>this rating upon visual evaluation and the<br>amount of rattling generated by the "drum<br>test" defined above.<br>Although retention can vary from plant<br>to plant and even within a plant, the overall<br>rating is correlatable with IND.<br>In crossing between lines, in early<br>generations there is a segregation of IND<br>plants and non-IND plants. In this case<br>the plot is given a rating of the majority of<br>plants while the plants selected can have a<br>higher rating, which is reflected in VISUAL<br>SEED RETENTION. The ratings that are<br>cited in this character are for plots, but<br>ratings of 7 or 8 are only given if over 90%<br>of the plants have the higher rating. |
| (26) IMPROVED NON-<br>DEHISCENCE TEST<br>An ND line that passes<br>the rattle test and has a<br>visual IND rating >6.99<br>is considered IND. A<br>method for traditional<br>breeding of an IND line<br>is described in U.S.<br>Pat. No. 8,080,707. ND<br>and IND lines should<br>not have id or gs<br>alleles. | S38 = IND<br>(All crops, all nurseries)<br>Subjective rating based on<br>the following values:<br>IND = Improved Non-<br>dehiscent line<br>ZZ = Line that does not<br>pass the improved non-<br>dehiscent test<br>Distribution within Sesaco<br>based on visual IND (Total<br>number of lines tested =<br>1,934 in all nurseries from<br>2005 to 2007)<br>IND = 9.5%<br>ZZ = 90.5% | Varieties were designated as IND after<br>they demonstrated the defined<br>characteristics with statistically significant<br>data. |
| (27) DAYS TO<br>FLOWERING<br>Number of days from<br>planting until 50% of the<br>plants are flowering | S38 = 45 days<br>(Uvalde nursery, 2011)<br>Value based on the<br>average of a minimum of<br>three plots of the number<br>of days (unit of measure:<br>days)<br>Distribution within Sesaco<br>based on lines in Uvalde<br>nursery in 2000-2001<br>(Total number of samples<br>tested = 1831)<br>low = 33 days; high = 89<br>days<br>1 = <44.2 days; 87.9%<br>2 = <55.4 days; 7.8%<br>3 = <66.6 days; 2.4%<br>4 = <77.8 days; 1.7%<br>5 = >77.7 days; 0.2%<br>avg. = 40.9 days, std = 6.3 | The vegetative phase in sesame is from<br>the time of planting to the start of<br>flowering.<br>This data is taken as a date and later<br>converted to number of days. Flowering is<br>defined as flowers that are open - not<br>buds.<br>COMMENTS: flowering can be<br>accelerated by drought and it can be<br>delayed by higher moisture and/or fertility.<br>Higher heat units will decrease the days to<br>flowering.<br>Some lines are photosensitive and will<br>only begin flowering at a certain number of<br>hours of daylight.<br>Start of flowering does not always<br>equate to start of capsule formation. Many<br>lines will flower and not set capsules from<br>the first flowers. |
| (28) DAYS TO<br>FLOWER<br>TERMINATION<br>Number of days from<br>planting until 90% of the<br>plants have stopped<br>flowering | S38 = 80 days<br>(Uvalde nursery, 2011)<br>Value based on the<br>average of a minimum of<br>three plots of the number<br>of days (unit of measure:<br>days)<br>Distribution within Sesaco<br>based on lines in Uvalde<br>nursery in 2000-2001 | The reproductive phase of sesame is<br>from the start to the end of flowering.<br>This data is taken as a date and later<br>converted to number of days. Flowering is<br>defined as flowers that are open - not<br>buds. At the end of the flowering period,<br>the rate that a plant puts on open flowers<br>is reduced. Thus, there can be more than<br>10% of plants with buds and still have<br>reached this measure since there will not |

TABLE II-continued

Characters Distinguishing the S38 Line

| Character | Rating | Methodology |
|---|---|---|
| | (Total number of samples tested = 2668) low = 61 days; high = 114 days 1 = <71.6 days; 21.1% 2 = <82.2 days; 61.5% 3 = <92.8 days; 15.9% 4 = <103.4 days; 0.8% 5 = >103.3 days; 0.8% avg. = 77.1 days, std = 6.9 | be more than 10% with open flowers on any one day. The measure is based on the number of plants and not the number of flowering heads. The branches will stop flowering before the main stem, and thus the plot will appear like there are more plants not flowering. COMMENTS: flower termination can be accelerated by lower moisture and/or fertility, and it can be delayed by higher moisture and/or fertility. Higher heat units will decrease the DAYS TO FLOWER TERMINATION. It is known that there are lines that stop flowering sooner than expected in northern latitudes, but it is not known if this is due to a shorter photoperiod or cool temperatures. |
| (29) DAYS TO PHYSIOLOGICAL MATURITY Number of days from planting until 50% of the plants reach physiological maturity | S38 = 101 days (Uvalde nursery, 2011) Value based on the average of a minimum of three plots of the number of days (unit of measure: days) Distribution within Sesaco based on lines in Uvalde nursery in 2000-2001 (Total number of samples tested = 2374) low = 77 days; high = 140 days 1 = <89.6 days; 16.8% 2 = <102.2 days; 58.0% 3 = <114.8 days; 23.6% 4 = <127.4 days; 1.4% 5 = >127.3 days; 0.2% avg. = 97.1 days, std = 7.1 | The ripening phase of sesame is from the end of flowering until physiological maturity. This data is taken as a date and later converted to number of days. Physiological maturity (PM) is defined as the point at, which ¾ of the capsules have seed with final color. In most lines, the seed will also have a seed line and tip that are dark. COMMENTS: The concept of physiological maturity in sesame was developed by M. L. Kinman (personal communication) based on the concept of determining the optimum time to cut a plant and still harvest 95-99% of the potential yield. When the seed has final color, the seed can germinate under the proper conditions. If the plant is cut at physiological maturity, most of the seed above the ¾ mark will go to final color and are mature enough to germinate, but will not have as much seed weight. Since in even a fully mature plant, there is less seed weight made at the top of the plant, this loss of seed weight does not seriously affect the potential seed weight of the plant. Although present harvest methods let the plants mature and go to complete drydown, PM is important because after that point, the crop is less susceptible to yield loss due to frost or disease. The PM is also important if the crop is to be swathed or harvest aids are to be applied. Physiological maturity can be accelerated by lower moisture and/or fertility, and it can be delayed by higher moisture and/or fertility. Higher heat units will decrease the days to physiological maturity. Cool weather can delay physiological maturity. |
| (30) DAYS TO DIRECT HARVEST Number of days from planting until there is enough drydown for direct harvest | S38 = NT Value based on the average of a minimum of three plots of the number of days (unit of measure: days) Distribution within Sesaco based on lines in all nurseries from 2004 through 2006 (Total number of samples tested = 1,998) low = 103 days; high = 161 days 1 = <114.6 days; 3.3% 2 = <126.2 days; 13.3% 3 = <137.8 days; 32.1% | The drying phase of sesame is from physiological maturity until direct harvest. This data is taken as a date and later converted to number of days. Direct harvest is defined as the date at which the plants are dry enough for combining seed at 6% or less moisture. Over 99% of the sesame in the world is harvested by hand before the plant completely dries down. The plants should be dry below where the cutter bar of the combine will hit the plants. In many lines, 15-20 cm from the ground can be green without an effect on the moisture of the seed. In taking the data on a plot, the plants at the aisle have more moisture and fertility available and will drydown later. The same is true for |

TABLE II-continued

Characters Distinguishing the S38 Line

| Character | Rating | Methodology |
|---|---|---|
| | 4 = <149.4 days; 44.2%<br>5 = >149.3 days; 7.2%<br>avg. = 136.7 days, std = 10.3 | plants within the plot that have a gap of half a meter between plants. These plants should be disregarded in taking the data. In addition, there are few farmer fields that dry down uniformly because of varying soils and moisture. There is a certain amount of green that can be combined and still attain the proper moisture. The amount of green allowable is also dependent on the humidity at the day of combining - the lower the humidity the higher the amount of allowable green.<br>COMMENTS: This date is the most variable in the number of days that define the phenology of sesame because weather is so important. In dry years with little rainfall, the plants will run out of moisture sooner and will dry down faster than in years with more rainfall. Fields that are irrigated by pivots will generally dry down faster than fields with flood or furrow irrigation because pivots do not provide deep moisture. Fields with less fertility will drydown faster than fields with high fertility. Fields with high populations will dry down faster than fields with low populations. In low moisture situations lines with a strong taproot will dry down later than lines with mostly shallow fibrous roots. |
| (31) LODGING TOLERANCE<br>The amount of lodging | S38 = NT<br>Average of a minimum of three plots of a subjective rating based on the following values:<br>0 to 8 rating<br>8 = no lodging<br>7 = Less than 5% of plants lodged<br>4 = 50% of plants lodged<br>1 = All plants lodged<br>Intermediate values are used.<br>Distribution within Sesaco based on lines in Uvalde and Lorenzo nurseries in 2007<br>(Total number of samples tested = 1061)<br>low = 1.0; high = 8.0<br>1 = <2.4; 3.1%<br>2 = <3.8; 6.9%<br>3 = <5.2; 22.6%<br>4 = <6.6; 18.9%<br>5 = >8.0; 48.4%<br>avg. = 6.1, std = 1.7 | The data is taken after physiological maturity (see DAYS TO PHYSIOLOGICAL MATURITY - Character No. 29) and before direct harvest (see DAYS TO DIRECT HARVEST - Character No. 30). Lodging that occurs after direct harvest in nurseries would not be a factor in commercial sesame.<br>There are three types of lodging: where the plants break at the stem, where the plants bend over but do not break, and where the plants uproot and bend over. When a plant breaks over, it will rarely produce any new seed, and the existing seed may or may not mature. If there is a total break, there is no hope, but if there is still some active stem translocation through the break, there can be some yield recovery. The main causes for uprooting of plants are shallow root systems and fields that have just been irrigated, creating a soft layer of soil. When a plant bends over early in development, some lines adapt better than others in terms of having the main stems turn up and continue flowering. The tips of the branches are usually matted under the canopy and will rarely turn up, but new branches can develop. As the plants go to drydown and the weight of the moisture is lost, many of the bent plants will straighten up making the crop easier to combine.<br>COMMENTS: The major cause of lodging is the wind. In areas where there are constant winds such as in Oklahoma and northern Texas, the plants adjust by adding more lignin to the stems. It takes a stronger wind to cause lodging than in those areas where there are normally only breezes (unless there is a strong front or thunderstorm that passes through). In areas with more root rot, the stems are weak and it takes little wind to lodge the plants. |

TABLE II-continued

Characters Distinguishing the S38 Line

| Character | Rating | Methodology |
|---|---|---|
| (32) SEED COLOR<br>The color of the seed coat | S38 = BF<br>(All crops, all nurseries)<br>Subjective rating based on the following values:<br>WH = White<br>BF = Buff<br>TN = Tan<br>LBR = Light brown<br>GO = Gold<br>LGR = Light gray<br>GR = Gray<br>BR = Brown<br>RBR = Reddish brown<br>BL = Black<br>Distribution within Sesaco based on seed harvested in all nurseries in 1982-2001 (Total number of samples tested = 161,809)<br>WH = 0.8%<br>BF = 74.8%<br>TN = 9.0%<br>LBR = 1.4%<br>GO = 1.5%<br>LGR = 0.6%<br>GR = 1.4%<br>BR = 6.5%<br>RBR = 0.6%<br>BL = 3.5% | This data is taken in the laboratory with the same lighting for all samples. The seed from the whole plant is used.<br>Seed coat color is taken on mature seeds. If there is any abnormal termination, the colors are not quite as even. The color of immature seed varies. Usually light seeded lines have tan to light brown immature seed; tan, light brown, gold, brown, light gray, and gray lines have lighter immature seed; black lines can have tan, brown, or gray immature seed. Usually, moisture, fertility, population and light intensity do not have an effect on seed coat color. Light colored seeds in a drought may have a yellowish tinge. Seeds in some lines in the tan, light brown and gold range can change from year to year among themselves. |
| (33) SEED WEIGHT -<br>100 SEEDS FROM THE ENTIRE PLANT<br>Weight of 100 seeds taken from the entire plant. | S38 = 0.305 g<br>(All experimental nurseries, 1997-2012)<br>Value based on the average of a minimum of three samples of the weight of 100 seeds from the 10 capsules (unit of weight: grams)<br>Distribution within Sesaco based on stable lines in all nurseries in 1997-2002 (Total number of lines tested = 820 with 2,899 samples)<br>low = 0.200 g; high = 0.455g<br>1 = <0.251 g; 10.1%<br>2 = <0.302 g; 48.4%<br>3 = <0.353 g; 34.0%<br>4 = <0.404 g; 7.2%<br>5 = >0.403 g; 0.2%<br>avg. = 0.298 g, std = 0.04 | Plants that are being carried further in research are selected individually or in bulk. The seed is then threshed and cleaned. Count out 100 seeds and weigh. The seed must be dry.<br>COMMENTS: The weight increases with higher moisture/fertility. Generally, the weight of the seed from the whole plant is lighter than the seed weight taken from the 10cap test. In previous patents, the seed size was determined from the middle of the main stem using the seed from the 10cap test samples. The change has been made since the seed from the entire plant is a better reflection of the size of the seed delivered to processors. |
| (34) COMPOSITE KILL TOLERANCE<br>The amount of plants killed by root rots in the Sesaco nurseries | S38 = 6.9<br>(All nurseries, 2011-2013)<br>Average of a minimum of three plots of a subjective rating based on the following values: Ratings are based on the number of plants killed in a plot. Before physiological maturity (PM), the following ratings are used:<br>1 = >90% kill before DAYS TO FLOWERING TERMINATION (Character No. 28)<br>2 = >90% kill between DAYS TO FLOWERING TERMINATION (Character No. 28) and DAYS TO PHYSIOLOGICAL MATURITY (Character No. 29) | On the week a plot reaches PM, a rating is assigned. The ratings are then taken for 2 additional weeks. The three ratings are averaged for a final kill rating. For example, if a plot has a final kill of 766, the average for the plot will be 6.33. When a value of 1 or 2 is assigned, there are no additional ratings and there is no averaging.<br>There are three root diseases that affect sesame in Texas: *Fusarium oxysporum*, *Macrophomina phaseoli*, and *Phytophthora parasitica*. Between 1988 and the present, spores of these three have been accumulated in one small area (1 square km) north of Uvalde, and thus is an excellent screening area for the diseases. Although each root rot disease attacks sesame in a different way and may result in different symptoms, no effort is made to definitively determine which disease is the etiological agent for the affected plants. |

TABLE II-continued

Characters Distinguishing the S38 Line

| Character | Rating | Methodology |
|---|---|---|
| | After PM, the following ratings are used:<br>3 = >90% kill<br>4 = 50 to 89% kill<br>5 = 25 to 49% kill<br>6 = 10 to 24% kill<br>7 = less than 10% kill<br>8 = no kill<br>Distribution within Sesaco based on lines in Uvalde nursery in 2000 -2001 (Total number of samples tested = 3045)<br>low = 1.00; high = 8.00<br>1 = <1.6; 1.7%<br>2 = <3.2; 16.7%<br>3 = <4.8; 38.7%<br>4 = <6.4; 31.2%<br>5 = >6.3; 11.6%<br>avg. = 4.52, std = 1.49 | Pathological screenings in the past have found all 3 pathogens present in dead plants.<br>COMMENTS: Normally, the ratings will decrease a maximum of one value per week. There is an overlap between any two ratings, but this is overcome to a certain extent by using three ratings over 2 weeks.<br>The amount of kill is usually increased with any type of stress to the plants. Drought can increase the amount of *Macrophomina*; too much water can increase the amount of *Phytophthora*; high temperatures and humidity can increase the amount of *Fusarium* and *Phytophthora*. High population can increase all three diseases.<br>The ratings for any one year can be used to compare lines grown in that year, but should not be used to compare lines grown in different years. The amount of disease in any one year is highly dependent on moisture, humidity, and temperatures. |
| (35) TOLERANCE TO *FUSARIUM* WILT (*F. oxysporum*)<br>Amount of tolerance to *Fusarium* wilt | S38 = NT<br>Average of a minimum of three plots of a subjective rating based on the following values:<br>0 to 8 scale of the % of infected plants<br>8 = Zero disease<br>7 = <10% infected<br>4 = 50% infected<br>1 = >90% infected<br>0 = all infected<br>Intermediate values are used.<br>NT = not tested<br>NEC = no economic damage - not enough disease to do ratings | Ratings can be done in several ways:<br>1. Take ratings after the disease is no longer increasing<br>2. Take ratings on consecutive weeks until disease is no longer increasing and average ratings.<br>3. Take periodic ratings and average ratings.<br>COMMENTS: *Fusarium* has been a problem in South Texas, particularly on fields that have been planted with sesame before. Normally, only the COMPOSITE KILL TOLERANCE (Character No. 34) rating is taken. |
| (36) TOLERANCE TO *PHYTOPHTHORA* STEM ROT (*P. parasitica*)<br>Amount of tolerance to *Phytophthora* stem rot | S38 = NT<br>Subjective rating<br>See Values for *Fusarium* | See Methodology for TOLERANCE TO *FUSARIUM* WILT (Character No. 35)<br>COMMENTS: *Phytophthora* has been a problem in Arizona and Texas, particularly on fields that have been over-irrigated. Normally, only the COMPOSITE KILL TOLERANCE (Character No. 34) rating is taken. |
| (37) TOLERANCE TO CHARCOAL ROT (*Macrophomina phaseoli*)<br>Amount of tolerance to Charcoal rot | S38 = NT<br>Subjective rating<br>See Values for *Fusarium* | See Methodology for TOLERANCE TO *FUSARIUM* WILT (Character No. 35)<br>COMMENTS: *Macrophomina* has been a problem in Arizona and Texas, particularly on fields that go into a drought. Normally, only the COMPOSITE KILL TOLERANCE (Character No. 34) rating is taken. |
| (38) TOLERANCE TO BACTERIAL BLACK ROT (*Pseudomonas sesami*)<br>Amount of tolerance to bacterial black rot | S38 = 5.3<br>(Lorenzo nursery, 2010)<br>Average of a minimum of three plots of a subjective rating based on the following values:<br>0 to 8 scale of the % of infected plants<br>8 = Zero disease<br>7 = <10% infected<br>4 = 50% infected<br>1 = >90% infected<br>0 = all infected<br>Intermediate values are used.<br>NT = not tested<br>NEC = no economic | See Methodology for TOLERANCE TO *FUSARIUM* WILT (Character No. 35)<br>COMMENTS: This disease occurs occasionally when there is continual rainy weather with few clouds. In most years, the disease abates once the weather changes. No economic damage has been noticed. |

TABLE II-continued

Characters Distinguishing the S38 Line

| Character | Rating | Methodology |
|---|---|---|
| | damage - not enough disease to do ratings Distribution within Sesaco based on lines in Uvalde nursery in 2004 (Total number of samples tested = 593) low = 4.00; high = 8.00 1 = <2.4; 0.0% 2 = <3.8; 0.0% 3 = <5.2; 8.6% 4 = <6.6; 16.0% 5 = >6.5; 75.4% avg. = 7.13, std = 1.00 | |
| (39) TOLERANCE TO SILVERLEAF WHITEFLY (*Bemisia argentifolii*) Amount of tolerance to the silverleaf whitefly | S38 = NT Average of a minimum of three plots of a subjective rating based on the following values: 0 to 8 scale of the % of infected plants 0 to 8 scale 8 = Zero insects 7 = Few insects 4 = Many insects 1 = Insects killing the plants Intermediate values are used. NT = not tested NEC = no economic damage - not enough insects to do ratings | Ratings can be done in several ways: 1. Take ratings after the insects are no longer increasing. 2. Take ratings on consecutive weeks until insects are no longer increasing and average ratings. 3. Take periodic ratings and average ratings. COMMENTS: there have been very few years (1991-1995) where the incidence of silverleaf whitefly has affected nurseries or commercial crops. In most years, a few whiteflies can be seen in the sesame with no economic damage. In the middle 1990s, the USDA began introducing natural predators of the silverleaf whitefly in the Uvalde area. It is not known if the predators reduced the effects of the whitefly or there is a natural tolerance to whitefly in the current varieties. Higher temperatures decrease the number of days between generations. There are indications that higher moisture and fertility increase the incidence of whiteflies, but there is no definitive data. The sweet potato whitefly (*Bemisia tabaci*) has been observed in nurseries since 1978 without any economic damage. |
| (40) TOLERANCE TO GREEN PEACH APHIDS (*Myzus persicae*) Amount of tolerance to the green peach aphid | S38 = NT Subjective rating; see Values for Whitefly Distribution within Sesaco based on lines in Uvalde nursery in 2004 (Total number of samples tested = 412) low = 1.00; high = 8.00 1 = <2.4; 1.0% 2 = <3.8; 0.5% 3 = <5.2; 10.7% 4 = <6.6; 4.8% 5 = >6.5; 83.0% avg. = 7.04, std = 1.35 | See Methodology for TOLERANCE TO SILVERLEAF WHITEFLY (Character No. 39) COMMENTS: There have been very few years (1990-1995) where the incidence of green peach aphid has affected nurseries or commercial crops. In most years, a few aphids can be seen in the sesame with no economic damage. There have been many years in West Texas when the cotton aphid has decimated the cotton and did not build up on adjacent sesame fields. Higher moisture and fertility increase the susceptibility to aphids. |
| (41) TOLERANCE TO POD BORERS (*Heliothis* spp.) Amount of tolerance to pod borers | S38 = NT Subjective rating; see Values for Whitefly | See Methodology for TOLERANCE TO SILVERLEAF WHITEFLY (Character No. 39) COMMENTS: There have been very few years (1985) where the incidence of *Heliothis* has affected nurseries or commercial crops. In most years, a few borers can be seen in the sesame with no economic damage. |
| (42) TOLERANCE TO ARMY WORMS (*Spodoptera* spp.) Amount of tolerance to army worms | S38 = NT Subjective rating; see Values for Whitefly | See Methodology for TOLERANCE TO SILVERLEAF WHITEFLY (Character No. 39) COMMENTS: There have been very few years (1984-1987) where the incidence of *Spodoptera* has affected commercial crops in Arizona. In Texas, army worms have decimated cotton and alfalfa fields next to sesame without any |

TABLE II-continued

Characters Distinguishing the S38 Line

| Character | Rating | Methodology |
|---|---|---|
| (43) TOLERANCE TO CABBAGE LOOPERS (*Pieris rapae*) Amount of tolerance to cabbage loopers | S38 = NT (Lorenzo nursery 2007) Subjective rating; see values for Whitefly | damage to the sesame. It is not known if the Arizona army worm is different from the Texas army worm. See Methodology for TOLERANCE TO SILVERLEAF WHITEFLY (Character No. 39) COMMENTS: There have been very few years (1992-1993) where the incidence of cabbage loopers has affected nurseries. In commercial sesame, cabbage loopers have been observed with no economic damage. |
| (44) PRESENCE OF PYGMY ALLELES The pygmy allele is a new recessive gene that affects the growth of the sesame plant. | S38 = PY/PY (All crops; all nurseries) py/py = homozygous pygmy alleles PY/py = heterozygous pygmy alleles PY/PY= normal (no pygmy alleles) Distribution within Sesaco based on stable lines in the collection as of 2009 (Total number of lines = 40,715) py/py = 145 PY/py = 629 Normal = 39,941 | In the homogygous condition. The pygmy allele (py) reduces the HEIGHT OF THE PLANT (Character No. 5), the HEIGHT OF THE FIRST CAPSULE (Character No. 6), and the AVERAGE INTERNODE LENGTH WITHIN CAPSULE ZONE (Character No. 9). In the heterozygous state, there are no reductions in the characters. In a cross between a homozygous pygmy and a normal, the pygmy allele is a recessive gene that will not show the shorter heights and internode lengths until segregating in the F2 generation, with no intermediates in the pygmy and the normal line. A homozygous pygmy selected in the F2, from the F3 generation on is pure in its effects on the three characters. Within pygmy lines there are differences in the 3 characters, but all of the pygmies differ from the normal lines. The name "pygmy" was chosen because these lines are shorter than dwarf lines that have been in the world germplasm for many years. The dwarf lines share the same three characters, but there are intermediates in the F2 generation and rarely any plants as short as the original dwarf. |
| (45) SEED OIL CONTENT The percentage of oil in the seed. | S38 = 53.1% (Uvalde nursery, 2010) 52.5% (Uvalde nursery, 2011) Value based on the average of a minimum of three samples of the percentage of oil in the seed (unit of measure: Actual number expressed as a percentage.) Distribution within Sesaco based on lines in Uvalde nursery in 2010-2011 (Total number of samples tested = 2,015) low = 36.0; high = 59.3 1 = <45; 0.8% 2 = <48; 4.8% 3 = <51; 27.4% 4 = <54; 47.4% 5 = >53.9; 19.6% avg. = 51.92, std = 2.52 | The data is taken after the seed has been cleaned of all extraneous material and is less than 6% moisture. There are two methodologies for determining oil content: laboratory analysis as prescribed in the procedures of the American Oil Chemists' Society (AOCS) or with a nuclear magnetic resonance (NMR) machine. The AOCS procedure does not remove all of the oil from the seed and thus has a lower content than with the NMR procedure. The NMR procedure is preferred because (1) it is non-destructive and (2) oil processors use that procedure. |

[a]Uvalde nursery planted north of Uvalde, Texas (latitude 29°22' north, longitude 99°47' west, 226 m elev) in middle to late May to early June from 1988 to the present; mean rainfall is 608 mm annually with a mean of 253 mm during the growing season; temperatures range from an average low of 3° C. and an average high of 17° C. in January to an average low of 22° C. and an average high of 37° C. in July. The nursery was planted on 96 cm beds from 1988 to 1997 and on 76 cm beds from 1998 to the present. The nursery was pre-irrigated and has had 2-3 post-plant irrigations depending on rainfall. The fertility has varied from 30-60 units of nitrogen.
[b]Rio Hondo nursery planted east of Rio Hondo, Texas (latitude 26°14' north, longitude 97°34' west, 8 m elev) in early April from 2010 to the present, mean rainfall is 715 mm annually with a mean of 323 mm during the growing season; temperatures range from an average low of 9° C. and an average high of 20° C. in January to an average low of 24° C. and an average high of 35° C. in July. The nursery was planted on 81 cm beds. The nursery was rainfed. The fertility was 80 units of nitrogen.
[c]Lorenzo nursery planted southeast of Lubbock, Texas (latitude 33°40' north, longitude 101°49' west, 1000 m elev) in mid-June from 2004 to the present; mean rainfall is 483 mm annually with a mean of 320 mm during the growing season; temperatures range from an average low of −4° C. and an average high of 11° C. in January to an average low of 20° C. and an average high of 33° C. in July. The nursery was planted on 101 cm beds. The nursery was rainfed. The fertility was 30 units of nitrogen.

In developing sesame varieties for the United States, there are eight characters that are desirable for successful crops: SHAKER SHATTER RESISTANCE (Character No. 22), IMPROVED NON-DEHISCENT VISUAL RATING (Character No. 25), COMPOSITE KILL TOLERANCE (Character No. 34), DAYS TO PHYSIOLOGICAL MATURITY (Character No. 29), YIELD AT DRYDOWN (Character 10), SEED COLOR (Character No. 32), SEED WEIGHT–100 SEEDS FROM THE ENTIRE PLANT (Character No. 33), and SEED OIL CONTENT (Character No. 45). The first four characters contribute to YIELD AT DRYDOWN, which is the most important economic factor normally considered by a farmer in the selection of a variety. The last three characters determine the market value of the seed.

SHAKER SHATTER RESISTANCE and IMPROVED NON-DEHISCENT VISUAL RATING determine how well the plants will retain the seed while they are drying down in adverse weather.

COMPOSITE KILL TOLERANCE determines whether the plants can finish their cycle and have the optimum seed fill.

DAYS TO PHYSIOLOGICAL MATURITY determines how far north and to which elevation the varieties can be grown.

In improving the characters, the YIELD AT DRYDOWN has to be comparable to or better than current varieties, or provide a beneficial improvement for a particular geographical or market niche.

In the United States and Europe, the SEED COLOR is important since over 95% of the market requires white or buff seed. There are limited markets for gold and black seed in the Far East. All other colors can only be used in the oil market.

SEED WEIGHT–100 SEEDS FROM THE ENTIRE PLANT determines the market for the seed. Lack of Composite kill Tolerance can reduce SEED WEIGHT–100 SEEDS FROM THE ENTIRE PLANT. In parts of the United States where there is little rain in dry years, the lack of moisture can reduce the SEED WEIGHT–100 SEEDS FROM THE ENTIRE PLANT.

SEED OIL CONTENT determines the market for the seed. Lack of Composite kill Tolerance can reduce SEED OIL CONTENT. Low fertility in terms of nitrogen raises SEED OIL CONTENT and high fertility lowers SEED OIL CONTENT.

There are other characters important in developing commercial sesame varieties explained in Langham, D. R. and T. Wiemers, 2002. "Progress in mechanizing sesame in the US through breeding", In: J. Janick and A. Whipkey (ed.), Trends in new crops and new uses, ASHS Press, Alexandria, Va. BRANCHING STYLE (Character No. 1), HEIGHT OF PLANT (Character No. 5) and HEIGHT OF FIRST CAPSULE (Character No. 6) are important in combining. CAPSULE ZONE LENGTH (Character No. 7), NUMBER OF CAPSULE NODES (Character No. 8), AVERAGE INTERNODE LENGTH WITHIN CAPSULE ZONE (Character No. 9), and SEED WEIGHT PER CAPSULE (Character No. 18) are important in creating potential YIELD AT DRYDOWN (Character No. 10). LEAF DIMENSIONS (Characters No. 12, 13, 14, and 15) are important in determining optimum populations.

NUMBER OF CAPSULES PER LEAF AXIL (Character No. 2), NUMBER OF CARPELS PER CAPSULE (Character No. 16), CAPSULE LENGTH (Character No. 17), CAPSULE WEIGHT PER CAPSULE (Character No. 19), and CAPSULE WEIGHT PER CM OF CAPSULE (Character No. 20) are important in breeding for VISUAL SEED RETENTION (Character No. 21) and IMPROVED NON-DEHISCENT VISUAL RATING (Character No. 25), which lead to testing for SHAKER SHATTER RESISTANCE (Character No. 22) and determining the CAPSULE SHATTERING TYPE (Character No. 23), NON-DEHISCENT TEST (Character 24) and IMPROVED NON-DEHISCENT TEST (Character No. 26).

DAYS TO FLOWERING (Character No. 27), DAYS TO FLOWER TERMINATION (Character No. 28), DAYS TO PHYSIOLOGICAL MATURITY (Character No. 29) and MATURITY CLASS (Character No. 3) are highly correlated and important in determining the phenology and geographical range for the variety.

DAYS TO DIRECT HARVEST (Character No. 30) is important in that once the plants reach physiological maturity there is no weather event that will increase yield and many weather events that may substantially lower the yield. A shorter drying phase increases yield. Presently, harvest aids have been approved by the Environmental Protection Agency for use on sesame. The harvest aids are applied at physiological maturity leading to early drydown. The days to direct harvest is not as important as in the past. PLANT PHENOTYPE (Character No. 4) is a summary character of characters 1, 2, and 3 that allows an overall visualization of the line.

TOLERANCE TO DROUGHT (Character No. 11) may reduce yield and seed weight. Even though there was a drought in the growing areas in 2006, there has not been a drought in nurseries planted since 2000 because of irrigation. LODGING TOLERANCE (Character No. 31) is important in years when there are high winds in the growing areas. The tolerance characters (Characters No. 35, 36, 37, 38, 39, 40, 41, 42, and 43) are important in reducing the losses from diseases and pests.

Over the past 37 years, Sesaco has tested 2,990 introductions from all over the world. Commercial samples have been obtained from China, India, Sudan, Ethiopia, Burkina Faso, Nigeria, Mozambique, Pakistan, Myanmar, Bangladesh, Vietnam, Egypt, Mexico, Guatemala, Nicaragua, Venezuela, Thailand, Turkey, Upper Volta, Uganda, Mali, Kenya, Indonesia, Sri Lanka, Afghanistan, Philippines, Colombia, Ivory Coast, Gambia, Somalia, Eritrea, Paraguay, Bolivia, and El Salvador. Additional research seed has been received from the commercial countries and from many other countries such as Australia, Iraq, Iran, Japan, Russia, Jordan, Yemen, Syria, Morocco, Saudi Arabia, Angola, Argentina, Peru, Brazil, Cambodia, Laos, Sri Lanka, Ghana, Gabon, Greece, Italy, South Korea, Libya, Nepal, Zaire, England and Tanzania. Research seed received from one country may have originated from another unspecified country. All of the commercial and research introductions have CAPSULE SHATTERING TYPE (Character No. 23) of shattering, "SHA".

Using selected characters from Table II, Table III provides a character differentiation between S38 and name cultivars from all over the world.

TABLE III

Character Differentiation of Various Sesame Varieties [a]

| Character | Rating | Name cultivars tested by Sesaco |
|---|---|---|
| CAPSULE SHATTERING TYPE (Character No. 23) | SHA | Eliminate the following from the world: From Venezuela: Venezuela 51, Venezuela 52, Guacara, Aceitera, Inamar, Acarigua, Morada, Capsula Larga, Arawaca, Piritu, Glauca, Turen, DV9, Fonucla, UCLA From Mexico: Pachequeno, Yori, Anna, Teras, Denisse, Canasta, Tehvantepeter From India: TMV1, TMV3 From Turkey: Ozberk, Muganli, Gamdibi, Marmara From Israel: DT45 From Guatemala: R198, R30 From Paraguay: Escoba and INIA. From Texas: Llano, Margo, Dulce, Blanco, Paloma, Oro, Renner 1 and 2, Early Russian From California: UCR3, UCR4, Eva, Calinda (Cal Beauty) From Thailand: KU18 From Korea: Danback, Gwansan, Pungyiong, Suweon, Yuseong, Hanseon, Ahnsan, Kwangsan, Jinback, Pungsan, Sodan, Yangheuk, Konheuk, Whaheuck, Sungboon |

TABLE III-continued

Character Differentiation of Various Sesame Varieties [a]

| Character | Rating | Name cultivars tested by Sesaco |
|---|---|---|
| | SSH | Eliminate from Sesaco: S02, S03, S04, S05, S06, S07, S08, S09, S10, S12, S14 |
| | ID | Eliminate, the following from the world: From Venezuela: G2, Morada id From Texas: Rio, Delco, Baco, Improved Baco, Roy, Eli From South Carolina: Palmetto From California: UCR234 From Sesaco: S01 |
| | SR | All others, go to NON-DEHISCENT TEST |
| NON-DEHISCENT TEST (Character No. 24) | XX | Eliminate from Sesaco: S11, S15, S16, S17, S18, S19, S20, S21 |
| | ND | All others to the SEED COLOR |
| SEED COLOR (Character No. 32) | BL | Eliminate from Sesaco: S55 |
| | BF | All others to the IMPROVED NON-DEHISCENT TEST |
| IMPROVED NON-DEHISCENT TEST (Character No. 26) | ZZ | Eliminate from Sesaco: 11W, 19A, S22, S23, S24, S25, S26, S28, S29, (all of these lines and varieties have been disclosed in previous patents, and there are no lines or varieties that are not included.) |
| | IND | go to the PRESENCE OF PYGMY ALLELES |
| PRESENCE OF PYGMY ALLELES (Character No. 44) | py/py | Eliminate from Sesaco: S70 |
| | PY/PY | From Sesaco: S27, S30, S32, S33, S34, S35, S36, and S38, go to BRANCHING STYLE |
| BRANCHING STYLE (Character No. 1) | U | Eliminate from Sesaco: S30 and S34 |
| | B | From Sesaco: S27, S32, S33, S35, S36, S37 S38 and S39, go to Table IV |

[a] SHA = shattering; SSH = semi-shattering; ID = indehiscent, SR = shatter resistant; XX = not non-dehiscent according to the teachings of U.S. Pat. No. 6,100,452; ND = non-dehiscent according to the teachings of U.S. Pat. No. 6,100,452; IND = improved non-dehiscent according to the teachings of U.S. Pat. No. 8,080,707, py/py = presence of homozygous pygmy alleles; PY/PY = absence of pygmy alleles according to the teachings of U.S. patent Publication No. 2011/0271359; U = unbranched; B = branched Table III differentiates S38 from all other cultivars and varieties except S27, S32, S33, S35, S36, S37, and S39. Table IV provides additional data that separates S38 from S27, S32, S33, S35, S36, S37, and S39.

TABLE IV

Character Comparison of S38 to S27, S32, S33, S35 S36, 37 and 39

| No. | Character | Year/nursery | S27 | S32 | S33 | S35 | S36 | S37 | S38 | S39 |
|---|---|---|---|---|---|---|---|---|---|---|
| 6 | HEIGHT OF FIRST CAPSULE (cm) | 2013 UV | NT | 51 | 54 | 42 | 54 | 57 | 69 | 54 |
| 7 | CAPSULE ZONE LENGTH (cm) | 2013 UV | NT | 69 | 75 | 78 | 75 | 84 | 57 | 81 |
| 9 | AVERAGE INTERNODE LENGTH WITHIN CAPSULE ZONE (cm) | 2013 UV | NT | 2.4 | 2.6 | 2.8 | 3.3 | 3.0 | 1.7 | 3.0 |
| 17 | CAPSULE LENGTH (cm) | 1997-2011 | 2.18 | 2.14 | 2.09 | 2.20 | 2.19 | 2.10 | 2.31 | 1.96 |
| 18 | SEED WEIGHT PER CAPSULE (g) | 1997-2011 | 0.212 | 0.219 | 0.202 | 0.197 | 0.228 | 0.225 | 0.244 | 0.209 |

The essential differences between S38 and the other branched varieties are the HEIGHT OF FIRST CAPSULE, CAPSULE ZONE LENGTH, AVERAGE INTERNODE LENGTH WITHIN CAPSULE ZONE, CAPSULE LENGTH, AND SEED WEIGHT PER CAPSULE. The first capsule starts higher than the other varieties resulting in a shorter capsule zone. However, with a shorter internode length, longer capsules, and higher seed weight per capsule, the variety is able to compete in yield.

Table V shows all the characters from Table II for S38 and the current branched varieties S28, S32, S35, S36, S37, and S39. The table is in terms of all of the characters listed in Table II. The major differences in Table V are indicated in the "Dif" column by a "C" for commercially important differences and an "M" for morphological differences.

TABLE V

Character Comparison of S28, S32, S35, S36, S37, 38 and S39[a]

| No. | Character | Year/nursery | S28 | S32 | S35 | S36 | S37 | S38 | S39 | Dif |
|---|---|---|---|---|---|---|---|---|---|---|
| 1 | Branching Style | All | B | B | B | B | B | B | B | |
| 2 | Number of Capsules per Leaf Axil | All | 1 | 1 | 1 | 1 | 1 | 1 | 1 | |
| 3 | Maturity Class | Adjusted PM | 100 | 99 | 100 | 101 | 103 | 103 | 99 | |
| | | 2008-2013 UV | M | M | M | M | M | M | M | |
| 4 | Plant Phenotype | All | B1M | B1M | B1M | B1M | B1M | B1M | B1M | |
| 5 | Height of Plant (cm) | 2013 UV | 126 | 120 | 120 | 129 | 141 | 126 | 135 | |
| 6 | Height of First Capsule (cm) | 2013 UV | 51 | 51 | 42 | 54 | 57 | 69 | 54 | M |
| 7 | Capsule Zone Length (cm) | 2013 UV | 75 | 69 | 78 | 75 | 84 | 57 | 81 | M |
| 8 | Number of Capsule Node pairs | 2013 UV | 27 | 29 | 28 | 33 | 28 | 32 | 28 | |
| 9 | Average Internode Length within Capsule Zone (cm) | 2013 UV | 2.8 | 2.4 | 2.8 | 3.3 | 3.0 | 1.7 | 3.0 | M |
| 10 | Yield at Drydown (kg/ha) | 2013 UV | 1,504 | 1,485 | 1,647 | 1,570 | 1,664 | 1,487 | 1,347 | |
| | | 2013 RH | 1,265 | 1,109 | 1,261 | 1,416 | 1,490 | 1,388 | 1,539 | |
| 11 | Tolerance to Drought | | NT | NT | NT | NT | NT | NT | NT | |
| 12 | Leaf Length (cm) | 5th - 2008 UV | 23.0 | 25.5 | NT | NT | NT | NT | NT | |
| | | 10th - 2008 UV | 18.0 | 18.3 | NT | NT | NT | NT | NT | |
| | | 15th - 2008 UV | 13.7 | 14.1 | NT | NT | NT | NT | NT | |
| 13 | Leaf Blade Length (cm) | 5th - 2008 UV | 13.8 | 14.8 | NT | NT | NT | NT | NT | |
| | | 10th - 2008 UV | 14.4 | 14.7 | NT | NT | NT | NT | NT | |
| | | 15th - 2008 UV | 11.5 | 12.2 | NT | NT | NT | NT | NT | |
| 14 | Leaf Blade Width (cm) | 5th - 2008 UV | 18.0 | 13.8 | NT | NT | NT | NT | NT | |
| | | 10th - 2008 UV | 3.6 | 3.0 | NT | NT | NT | NT | NT | |
| | | 15th - 2008 UV | 2.0 | 1.6 | NT | NT | NT | NT | NT | |
| 15 | Petiole Length (cm) | 5th - 2008 UV | 9.2 | 10.7 | NT | NT | NT | NT | NT | |
| | | 10th - 2008 UV | 3.6 | 3.6 | NT | NT | NT | NT | NT | |
| | | 15th - 2008 UV | 2.3 | 2.0 | NT | NT | NT | NT | NT | |
| 16 | Number of Carpels per Capsule | All | 2 | 2 | 2 | 2 | 2 | 2 | 2 | |
| 17 | Capsule Length (cm) | 1997-2011 All | 2.27 | 2.14 | 2.20 | 2.19 | 2.10 | 2.31 | 1.96 | M |
| 18 | Seed Weight per Capsule (g) | 1997-2011 All | 0.228 | 0.219 | 0.197 | 0.228 | 0.225 | 0.244 | 0.209 | C |
| 19 | Capsule Weight per Capsule (g) | 1997-2011 All | 0.163 | 0.148 | 0.128 | 0.153 | 0.156 | 0.167 | 0.143 | |
| 20 | Capsule Weight per cm of Capsule (g) | 1997-2011 All | 0.072 | 0.069 | 0.058 | 0.070 | 0.074 | 0.072 | 0.073 | |
| 21 | Visual Shatter Resistance | All | W | I | I | I | I | I | I | |
| 22 | Shaker Shatter Resistance (%) | 1997-2011 All | 75.2 | 74.8 | 71.1 | 77.6 | 71.1 | 81.6 | 65.7 | |
| 23 | Capsule Shattering Type | All | SR | SR | SR | SR | SR | SR | SR | |
| 24 | Non-dehiscent Test | All | ND | ND | ND | ND | ND | ND | ND | |
| 25 | Improved Non-dehiscent visual rating | 2011 UV | | 7.08 | 7.44 | 7.37 | 7.29 | 7.33 | NT | |
| | | 2011 LO | 6.67 | 7.00 | 7.48 | 7.25 | 7.22 | 7.22 | 7.00 | |
| 26 | Improved Non-dehiscent Test | All | ZZ | IND | IND | IND | IND | IND | IND | |
| 27 | Days to Flowering | 2011 UV | 45 | 42 | 43 | 45 | 43 | 45 | 46 | |
| 28 | Days to Flower Termination | 2011 UV | 78 | 78 | 78 | 80 | 81 | 80 | 78 | |
| 29 | Days to Physiological Maturity | 2011 UV | 102 | 100 | 97 | 101 | 103 | 101 | 107 | |
| 30 | Days to Direct Harvest | | NT | NT | NT | NT | NT | NT | NT | |
| 31 | Lodging Tolerance | 2007 UV | 7.0 | 6.2 | NT | NT | NT | NT | NT | |
| | | 2007 LO | 5.3 | 7.1 | NT | NT | NT | NT | NT | |

TABLE V-continued

Character Comparison of S28, S32, S35, S36, S37, 38 and S39[a]

| No. | Character | Year/nursery | S28 | S32 | S35 | S36 | S37 | S38 | S39 | Dif |
|---|---|---|---|---|---|---|---|---|---|---|
| 32 | Seed Color | All | BF | BF | BF | BF | BF | BF | BF | |
| 33 | Seed Weight - 100 Seeds from the entire plant | 1997-2012 All | 0.293 | 0.284 | 0.302 | 0.315 | 0.284 | 0.305 | 0.297 | |
| 34 | Composite Kill Tolerance | 2011-2013 All | 7.0 | 6.5 | 6.8 | 6.6 | 6.3 | 6.9 | 6.7 | |
| 35 | Tolerance to Fusarium Wilt (*F. oxysporum*) | | NT | NT | NT | NT | NT | NT | NT | |
| 36 | Tolerance to Phytophthora Stem Rot (*P. parasitica*) | | NT | NT | NT | NT | NT | NT | NT | |
| 37 | Tolerance to Charcoal Rot (*Macrophomina phaseoli*) | | NT | NT | NT | NT | NT | NT | NT | |
| 38 | Tolerance to Bacterial Black Rot (*Pseudomonas sesami*) | 2010 LO | 7.0 | 7.0 | 7.0 | 5.0 | 6.3 | 5.3 | 7.0 | |
| 39 | Tolerance to Silverleaf Whitefly (*Bemisia argentifolii*) | 2011 PR | 5.0 | 5.0 | 5.7 | 4.0 | 4.0 | NT | 6.0 | |
| 40 | Tolerance to Green Peach Aphid (*Myzus persica*) | 2004 UV | 7.9 | 5.5 | NT | NT | NT | NT | NT | |
| 41 | Tolerance to Pod Borer (*Heliothis* spp.) | 2001 UV | NT | NT | NT | NT | NT | NT | NT | |
| 42 | Tolerance to Army Worms (*Spodoptera* spp.) | | NT | NT | NT | NT | NT | NT | NT | |
| 43 | Tolerance to Cabbage Loopers (*Pieris rapae*) | 2007 LO | NT | NEC | NT | NT | NT | NT | NT | |
| 44 | Presence of pygmy alleles | All | PY/PY | PY/PY | PY/PY | PY/PY | PY/PY | PY/PY | PY/PY | |
| 45 | Oil content (%) | 2010 UV | 52.9 | 52.4 | 51.7 | 53.5 | 53.2 | 53.1 | 53.5 | |
| | | 2011 UV | 52.0 | 53.7 | 54.1 | 53.5 | 51.9 | 52.5 | 50.5 | |

[a]B = true branches; U = uniculm (no true branches); UV = Uvalde nursery; M = medium maturity class of 95-104 days; B1M = phenotype of true branches, single capsules per leaf axil, and medium maturity class of 95-104 days; U1M = phenotype of uniculm, single capsules per leaf axil, and medium maturity class of 95-104 days; LO = Lorenzo nursery; NT = not tested; W = weather visual seed retention >75%; SR = shatter resistant; ND = non-dehiscent; ZZ = not improved non-dehiscent; IND = improved non-dehiscent; BF = buff color; and NEC = no economic damage - not enough disease or insects to do ratings; PY/PY = absence of pygmy alleles.

As stated earlier, in developing sesame varieties for the United States, there are eight important characters: SHAKER SHATTER RESISTANCE (Character No. 22), IMPROVED NON-DEHISCENT VISUAL RATING (Character No. 25), COMPOSITE KILL TOLERANCE (Character No. 34), DAYS TO PHYSIOLOGICAL MATURITY (Character No. 29), YIELD AT DRYDOWN (Character No. 10), SEED COLOR (Character No. 32), SEED WEIGHT–100 SEEDS FROM ENTIRE PLANT (Character No. 33), and SEED OIL CONTENT (Character No. 45). These characters will be discussed first comparing S38 to Sesaco varieties (S28, S30, S32, S34, S35, S36, S37, and S39, which are the current varieties used in the United States), followed by other characters that differentiate S38. The data is based on planting the varieties side by side with five replications in Uvalde, one in Rio Hondo, and two in Lorenzo.

Figure 2:
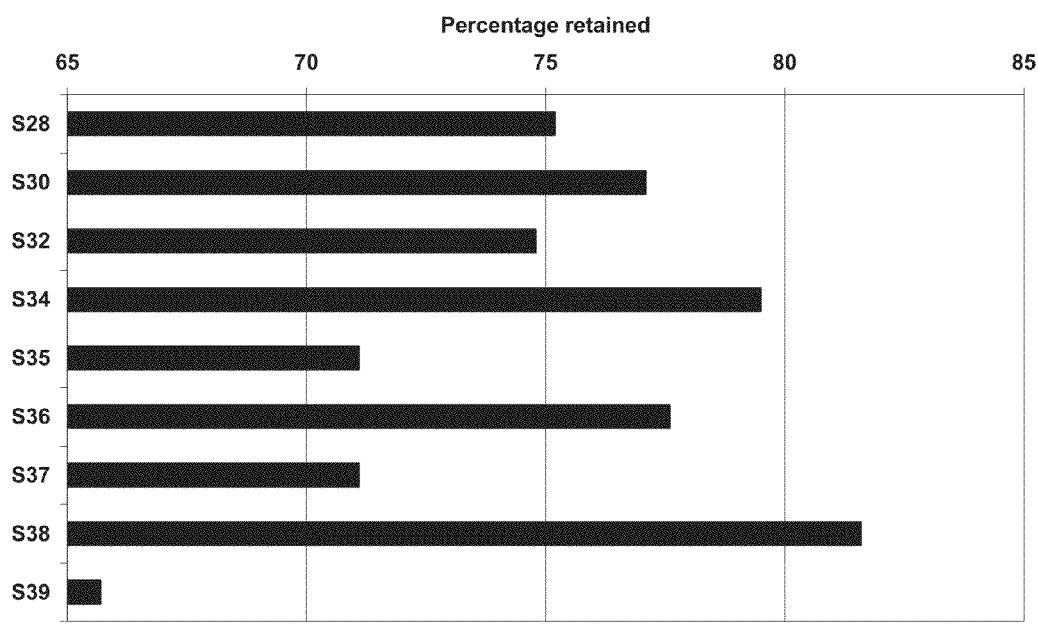
FIG. 2 through FIG. 10 compare Sesaco 38 (S38) to the present Sesaco varieties: Sesaco 28 (S28), Sesaco 30 (S30), Sesaco 32 (S32), Sesaco 34 (S34), Sesaco 35 (S35), Sesaco 36 (S36), Sesaco 37 (S37), and Sesaco 39 (S39).

FIG. 2 provides the SHAKER SHATTER RESISTANCE (Character No. 22) of various Sesaco sesame varieties using data from 1997 through 2011. SHAKER SHATTER RESISTANCE represents the amount of seed that is retained by the plant several months after being dry in the field. This standard was developed as a minimum standard in 1997-1998 and has proven to be a good predictor of shatter resistance. All varieties have SHAKER SHATTER RESISTANCE in the mid-sixty to mid-eighty percent level.

S38 has 81.6% SHAKER SHATTER RESISTANCE, which is above the 65% threshold established in U.S. Pat. No. 6,100,452 to qualify S38 as a non-dehiscent variety.

Figure 3:
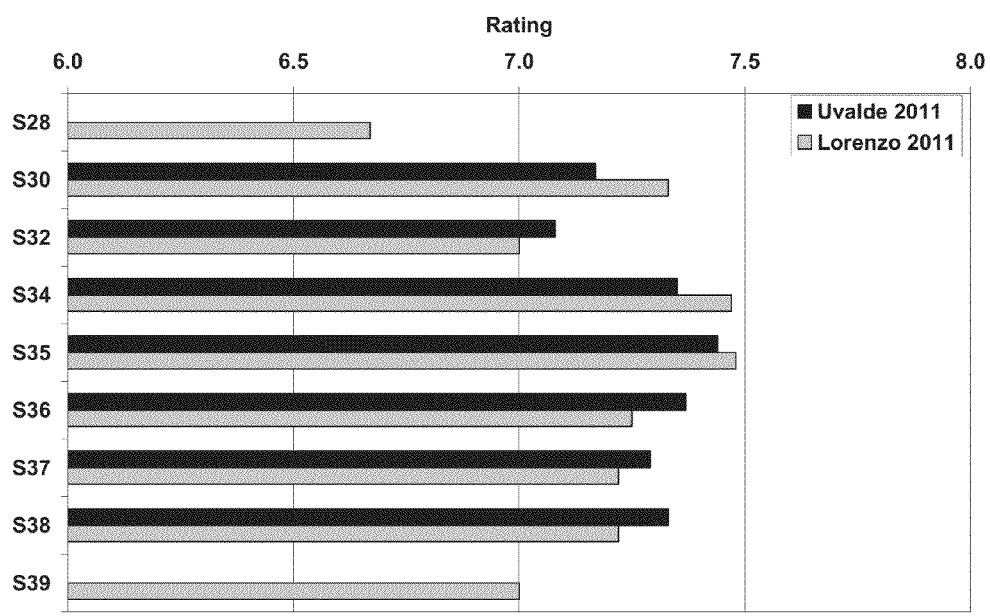

FIG. 3 provides the IMPROVED NON-DEHISCENT VISUAL RATING (Character No. 25) of the patented varieties (data from Uvalde and Lorenzo nurseries, 2011). When the plants have reached DAYS TO DIRECT HARVEST (Character No. 30), the plants are holding more than the seed represented by the SHAKER SHATTER RESISTANCE percentage. If there is no rain, fog, dew, or wind during the drying phase, the non-dehiscent plants will be retaining almost all of their seed for the combine. However, the predominant weather in the harvest season in the United States includes rain, fog, dew, and wind. The IMPROVED NON-DEHISCENT VISUAL RATING sets a new benchmark for selecting varieties based on a rating done 4 weeks after DAYS TO DIRECT HARVEST (the ideal harvest time).

S38 exhibited an IMPROVED NON-DEHISCENT VISUAL RATING of 7.33 (Uvalde nursery, 2011) and 7.22 (Lorenzo nursery, 2011) which are above the 7.0 threshold established in U.S. Pat. No. 8,080,707 to qualify S38 as an improved non-dehiscent variety.

Figure 4:
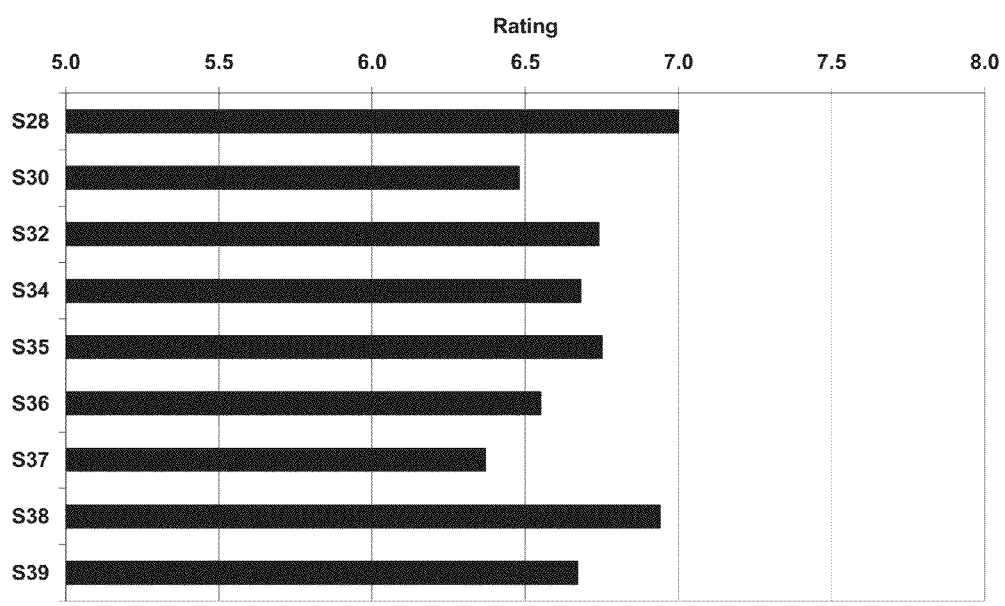

FIG. 4 provides the COMPOSITE KILL TOLERANCE (Character No. 34) of the current varieties (data from all nurseries 2011-2013). COMPOSITE KILL TOLERANCE is a composite rating of tolerance to three root rots: *Fusarium*, *Phytophthora*, and *Macrophomina*. In most years, *Fusarium* is the major cause of kill. When sesame is first introduced into a growing area, there are few disease problems, but over time the spores of these fungi accumulate and disease tolerance becomes important. When sesame was first introduced in Uvalde in 1988, the yields were high. As farmers planted on the same fields in subsequent years, the yields decreased.

S38 has a rating of 6.9 for COMPOSITE KILL TOLERANCE (data from all nurseries, 2011-2013) and is comparable to most of the other patented commercial varieties. Any rating above 5.67 indicates that over 90% of the plants produced good seed to the top of the plant.

Figure 5:
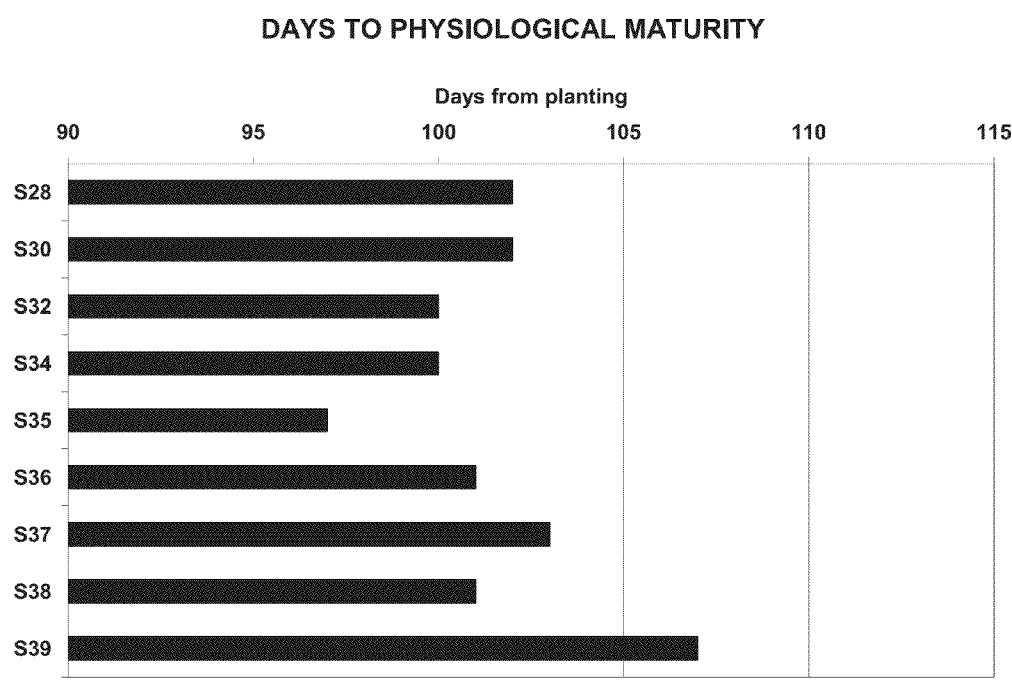

FIG. 5 provides the mean DAYS TO PHYSIOLOGICAL MATURITY (Character No. 29) of the current Sesaco sesame varieties (data from Uvalde nursery, 2011). In the United States, sesame is currently grown from South Texas to Central Kansas. The growing window of a crop is determined by the earliest the crop can be planted in the spring as the ground warms up, and the onset of cold weather in the fall. Current sesame varieties require about 21° C. ground temperature to establish an adequate population and night temperatures above 5° C. for normal termination. Generally, the ground is warm enough in South Texas in middle March and in Central Kansas in late May, and the night temperatures are warm enough in South Texas until the middle of November and in southern Kansas until the middle of October. The states to the east from Texas/Oklahoma/Kansas to the Atlantic are within the South Texas and Kansas extremes. Cold fronts may affect the growth of sesame, and these are more likely in northern growing areas from the middle of September on. Elevation may also affect the growing temperature. For example, moving from east of Lubbock, Tex., at the start of the Caprock toward the west, the elevations begin climbing approaching toward the Rocky Mountains. The higher the elevation, the earlier the onset of fall cold temperatures and the later the onset of spring warm temperatures. In all years, if the sesame is planted as early as temperatures allow, lines with DAYS TO PHYSIOLOGICAL MATURITY of 105 days or less will not be adversely affected by the temperatures, even in years with an early frost. Data gathered over a twenty-three year period indicates that about 96% of the time, sesame with a value of 115 or less DAYS TO PHYSIOLOGICAL MATURITY will produce a crop. Since most growing areas depend upon having a planting rain before the sesame is planted, the earlier the DAYS TO PHYSIOLOGICAL MATURITY of the variety, the more flexibility the farmers have with the planting date. Different geographical areas may have different goals due to the normal weather patterns. In South Texas, varieties with DAYS TO PHYSIOLOGICAL MATURITY of less than 110 days are generally suitable, while planting after 30 June in southern Kansas it is preferred, but not always necessary, to utilize varieties with lower DAYS TO PHYSIOLOGICAL MATURITY such as 100 days or less.

The mean DAYS TO PHYSIOLOGICAL MATURITY for S38 is 101, which allows it to be planted in all of the current sesame growing areas. Care should be taken in areas where early freezes may occur to plant S38 in at a time where it will physiologically mature prior to expected freezes.

Figure 6:
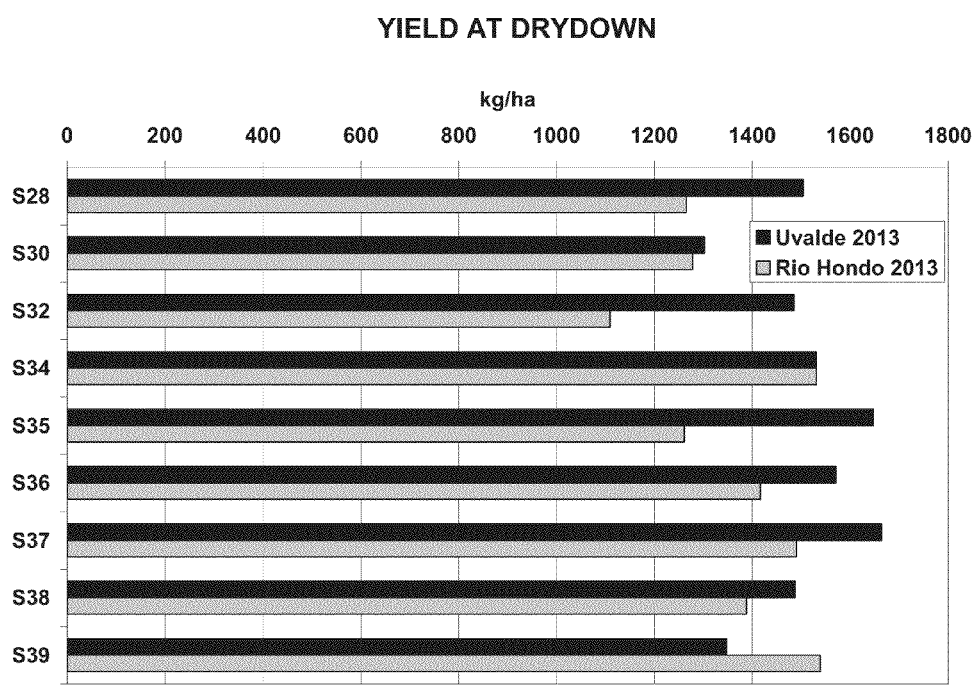

FIG. 6 provides the mean YIELD AT DRYDOWN (Character 10) of the patented varieties (testing in the Uvalde and Rio Hondo nurseries in 2013). In releasing a new variety, another important consideration is whether the yields will be comparable or better than the existing varieties.

The yield of S38 is expected to be comparable to that of prior varieties under typical growing conditions and was found to be comparable under less than ideal conditions used for testing as reported in FIG. 6. The yield data is taken close to DAYS TO DIRECT HARVEST (Character No. 30), which is the ideal time to harvest. However, weather in the fall in the sesame growing areas of the United States can prevent harvest for up to a month subjecting the crop to rain, fog, dew, and wind. Those four factors increase shattering, and wind may bring on lodging. Drought can affect yield. As reported in FIG. 6, the 2013 data from the Uvalde and Rio Hondo areas indicates that S38 with yields of 1,487 kg/ha (Uvalde nursery, 2013) and 1,388 kg/ha (Rio Hondo nursery, 2013) are comparable to the current varieties.

The SEED COLOR (Character No. 32) of S38 is buff, which is suitable for most of the U.S. and world markets.

Figure 7:
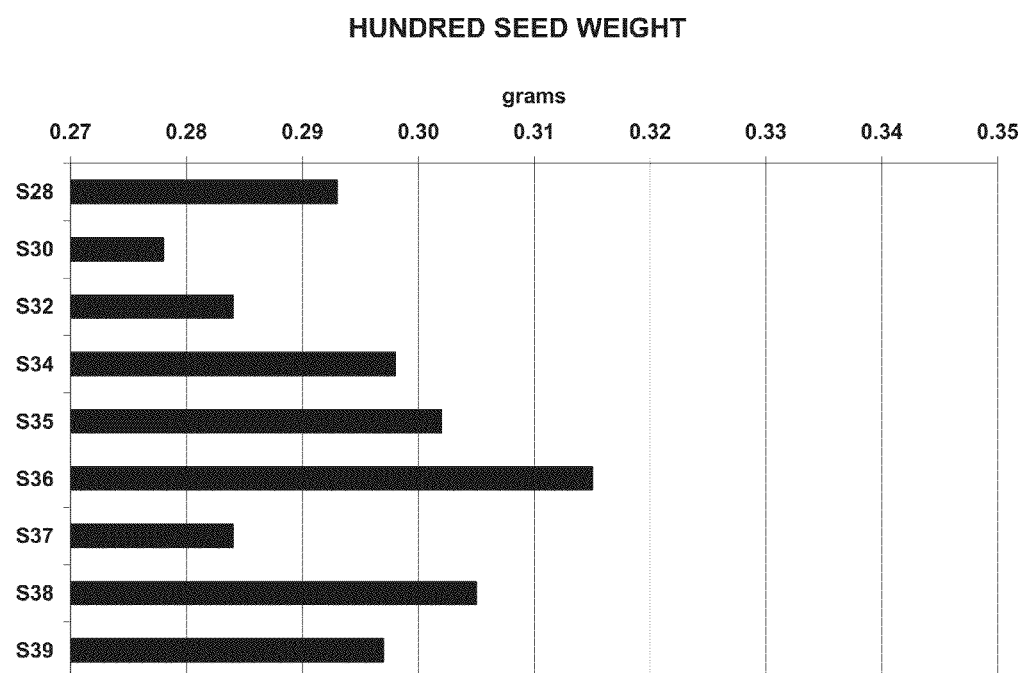

FIG. 7 provides the mean SEED WEIGHT–100 SEEDS FROM THE ENTIRE PLANT (Character No. 33) of the current varieties between 1997 and 2011. A particular seed weight may be a characteristic desired by certain seed processors and end-users and commercial specifications may require a threshold seed weight.

S38 seed is comparable to the other patented varieties (0.305 grams per hundred seeds), and thus meets most commercial specifications in the ingredient and natural topping markets for sesame seed, which (in the United States) often set a threshold value of 0.30 grams per hundred seed weight. S36 has the highest weight of all the varieties used commercially in the US.

Figure 8:
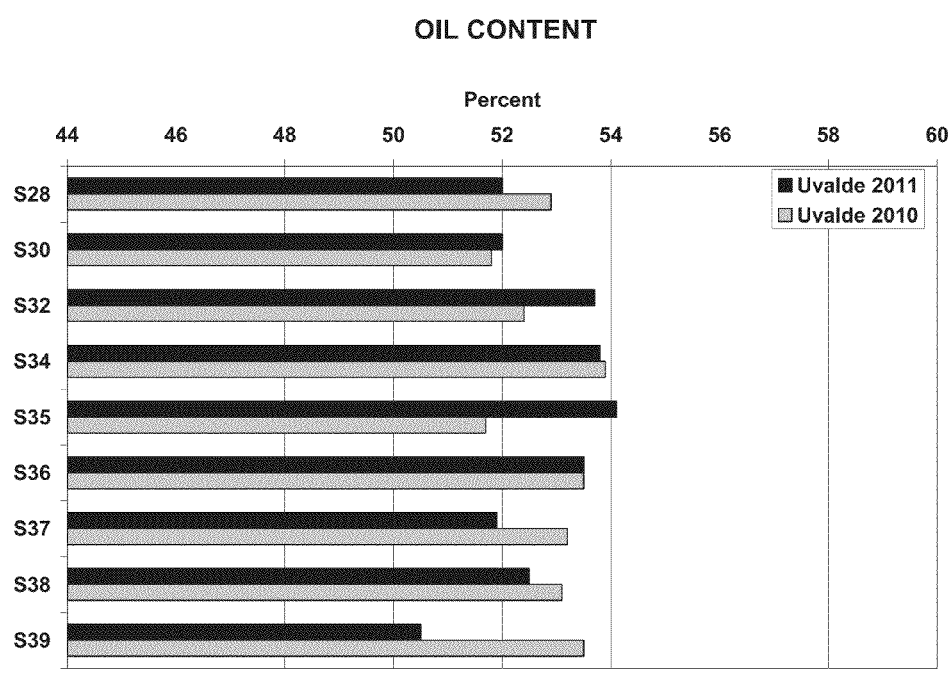

FIG. 8 provides the SEED OIL CONTENT (Character No. 45) of the current varieties. The commercial oil markets generally contractually require that sesame seed contain an oil content of at least 50-52%. If the oil content is lower than the specified requirement, the contract generally penalizes the seller. While current commercial practice does not include a monetary incentive to the seller if sesame seed has a higher oil content than the contractual requirement, increasing the oil content of sesame seed may provide de facto advantages to the purchaser or user.

S38 exhibited oil contents of 53.1% (data from Uvalde 2010) and 52.5% (Uvalde 2011) and thus is suitable for use as a source of sesame oil for the commercial oil market.

Figure 9:
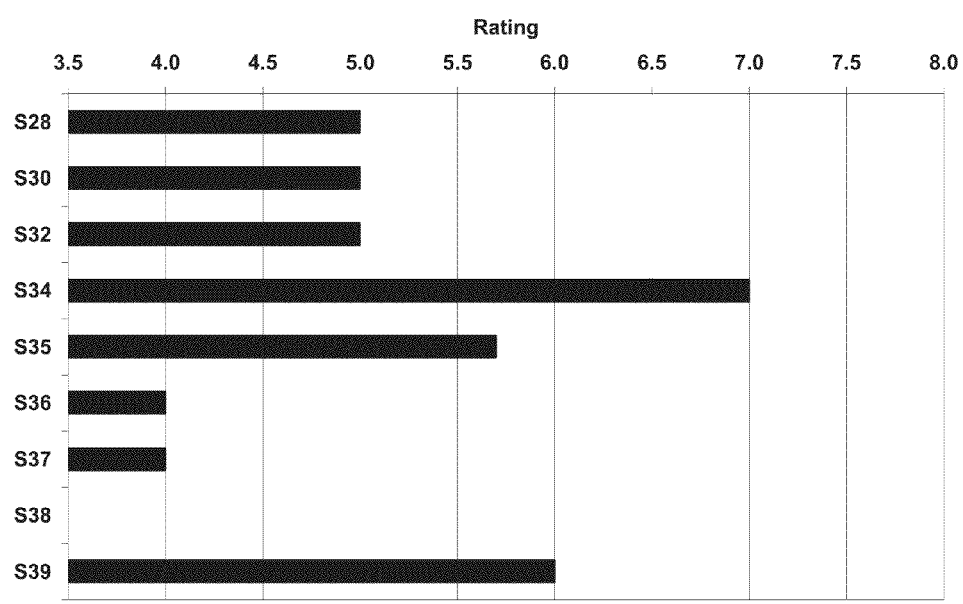

FIG. 9 provides the TOLERANCE TO SILVERLEAF WHITEFLY (Character No. 39). This pest is a problem in areas having high temperatures and other crops that attract whiteflies, such as vegetable crops. Examples of sesame growing areas which may be subject to whitefly issues are the South Texas/Lower Rio Grande Valley region, which typically has many acres of vegetables planted, and Puerto Rico. Having tolerance to the whitefly provides a benefit to a sesame variety.

S38 was not planted in the Puerto Rico 2011 nursery, but indications from Rio Hondo are that it is no better or worse than the current varieties.

Figure 10:
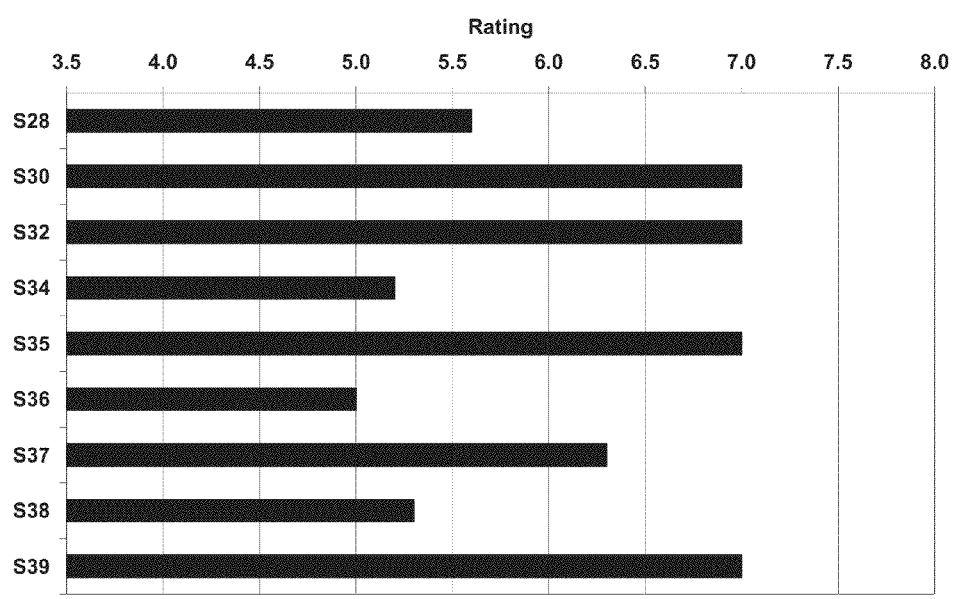

FIG. 10 provides the TOLERANCE TO BACTERIAL BLACK ROT (Character No. 38). Bacterial black rot may occur, though rare, when there are cool, cloudy days, usually at higher elevations. While there may be little sesame acreage subject to these conditions, tolerance may still be important to some growers.

S38, with a rating of 5.3 (Lorenzo 2010), exhibits less tolerance when these conditions are present than most previously described varieties.

On Mar. 13, 2014, a deposit of at least 2500 seeds of sesame plant S38 was made by Sesaco Corporation under the provisions of the Budapest Treaty with the American Type Culture Collection (ATCC), 10801 University Boulevard, Manassas, Va. 20110-2209, and the deposit was given ATCC Accession No. PTA-121090. This deposit will be maintained in the ATCC depository for a period of 30 years or 5 years after the last request or for the enforceable life of the patent, whichever is longer. Should the seeds from the sesame line S38 deposited with the American Type Culture Collection become non-viable, the deposit will be replaced by Sesaco Corporation upon request.

The foregoing invention has been described in some detail by way of illustration and characters for purposes of clarity and understanding. However, it will be obvious that certain changes and modifications may be practiced within the scope of the invention as limited only by the scope of the appended claims.

I claim:

1. A seed of sesame variety designated S38, a sample of said seed having been deposited under ATCC Accession No. PTA-121090.

2. A sesame plant produced by growing the seed of sesame variety S38, a sample of said seed having been deposited under ATCC Accession No. PTA-121090.

3. Pollen of said sesame plant of claim 2.

4. A sesame plant having all the physiological and morphological characteristics of sesame variety S38, a sample of the seed of said variety having been deposited under ATCC Accession No. PTA-121090.

5. A tissue culture of regenerable cells produced from seed of sesame variety S38, a sample of said seed having been deposited under ATCC Accession No. PTA-121090.

6. A tissue culture of regenerable cells produced from sesame plant S38 produced by growing the seed of sesame variety S38, a sample of said seed having been deposited under ATCC Accession No. PTA-121090.

7. A sesame plant regenerated from a tissue culture of regenerable cells produced from seed of sesame variety S38, a sample of said seed having been deposited under ATCC Accession No. PTA-121090, wherein said regenerated sesame plant has all the physiological and morphological characteristics of said sesame variety S38.

8. A sesame plant regenerated from a tissue culture of regenerable cells produced from a sesame plant produced by growing the seed of sesame variety S38, a sample of said seed having been deposited under ATCC Accession No. PTA-121090, wherein said regenerated sesame plant has all the physiological and morphological characteristics of said sesame variety S38.

9. A method of producing sesame seed, comprising crossing a first parent sesame plant with a second parent sesame plant and harvesting the resultant sesame seed, wherein said first or second parent sesame plant was produced by growing seed of sesame variety S38, a sample of said seed having been deposited under ATCC Accession No. PTA-121090.

* * * * *